(12) United States Patent
Boulet et al.

(10) Patent No.: US 10,045,934 B2
(45) Date of Patent: Aug. 14, 2018

(54) USE OF A PHOTOSYNTHETIC CELL EXTRACT COMPRISING FUNCTIONAL THYLAKOIDS IN COSMETIC COMPOSITIONS

(75) Inventors: Andre P. Boulet, Quebec (CA); Paul Maes, Vise (BE)

(73) Assignee: Groupe Sante Devonian, Montmagny, Quebec (CA)

( * ) Notice: Subject to any disclaimer, the term of this patent is extended or adjusted under 35 U.S.C. 154(b) by 1162 days.

(21) Appl. No.: 13/261,472

(22) PCT Filed: Apr. 12, 2011

(86) PCT No.: PCT/CA2011/000372
§ 371 (c)(1),
(2), (4) Date: Aug. 2, 2013

(87) PCT Pub. No.: WO2011/127559
PCT Pub. Date: Oct. 20, 2011

(65) Prior Publication Data
US 2013/0309181 A1 Nov. 21, 2013

(30) Foreign Application Priority Data
Apr. 2, 2011 (CA) .................... 2699676

(51) Int. Cl.
| | | |
|---|---|---|
| *A61K 8/97* | (2017.01) | |
| *A61K 8/99* | (2017.01) | |
| *A61K 36/00* | (2006.01) | |
| *A61Q 19/00* | (2006.01) | |
| *A61Q 19/08* | (2006.01) | |
| *A61Q 17/04* | (2006.01) | |

(52) U.S. Cl.
CPC .................. *A61K 8/97* (2013.01); *A61K 8/99* (2013.01); *A61K 36/00* (2013.01); *A61Q 17/04* (2013.01); *A61Q 19/004* (2013.01); *A61Q 19/08* (2013.01); *A61K 2800/522* (2013.01)

(58) Field of Classification Search
None
See application file for complete search history.

(56) References Cited

U.S. PATENT DOCUMENTS

2007/0036877 A1* 2/2007 Purcell ................. A61K 36/21
424/774

FOREIGN PATENT DOCUMENTS

| CA | 2393816 | 7/2001 |
|---|---|---|
| EP | 0688559 A1 | 12/1995 |
| WO | 01/49305 A2 | 7/2001 |
| WO | 03/004042 | 1/2003 |
| WO | 2005/027944 | 3/2005 |
| WO | 2010/008333 | 1/2010 |

OTHER PUBLICATIONS

Supplementary Partial European Search Report, dated Jul. 3, 2015, in related EP Appln. No. 11768299.
Agriculture and Agri-food Canada web site; News Release on Sep. 4, 2008; retrieved Jul. 15, 2011 http://www.agr.gc.ca/cb/index_e.php?s1-n&s2=2008&page=n80904.
Cosmeticsdesign-europe.com web site; Sep. 5, 2008; retrieved Jul. 15, 2011 http://www.cosmeticsdesign-europe.com/Formulation-Science/Canadian-govemment-backs-spinach-based-cosmetics.

* cited by examiner

*Primary Examiner* — Susan Coe Hoffman
(74) *Attorney, Agent, or Firm* — Hahn Loeser & Parks, LLP

(57) ABSTRACT

The invention relates to cosmetic and topical compositions containing an effective amount of a photosynthetic cell extract comprising a functional thylakoid system. The cosmetic compositions have anti-wrinkle and anti-aging effects on a user's skin. In addition, the photosynthetic cell extract protects skin against ultraviolet A (UVA) and ultraviolet (UVB) damage.

12 Claims, 30 Drawing Sheets

USE OF A PHOTOSYNTHETIC CELL EXTRACT COMPRISING FUNCTIONAL THYLAKOIDS IN COSMETIC COMPOSITIONS

FIELD OF THE INVENTION

The invention relates to cosmetic and topical compositions containing an effective amount of a photosynthetic cell extract comprising a functional thylakoid system. More specifically, it relates to cosmetic compositions having anti-wrinkle and anti-aging effects on a user's skin. The invention relates to the use of photosynthetic cell extract to protect skin against ultraviolet A (UVA) and ultraviolet (UVB) damage.

BACKGROUND OF THE INVENTION

The skin is a complex organ with 3 major tissue layers: the epidermis, dermis and hypodermis. Skin structure, as well as its different cell types, organization and role have been described in numerous publications. In order to understand the impact of substances such as drugs, natural extracts, and ultraviolet radiation on the skin, non-animal tests have been developed and are now used successfully in the study of skin damage/repair (Auger 2004; Rouabhia 1997; Van de Sandt 1999).

Anti-oxidants significantly prevent tissue damage and stimulate wound healing. This is done through numerous mechanisms including prevention/limitation of lipid peroxidation, inflammation and alteration of cell DNA. Some plant extracts are believed to have strong anti-oxidant effects (Thang 2001).

Thylakoids are specialized membranes that are responsible for photosynthesis in eukaryotes (plant and algae) and prokaryotes (bacteria). These photosynthetic organisms convert $CO_2$ to organic material by reducing this gas to carbohydrates in a complex set of reactions. Electrons for this reduction reaction ultimately come from water, which is then converted to oxygen and protons. Energy for this process is provided by light, which is absorbed by pigments (primarily chlorophylls and carotenoids).

The skin is an interface between the body and the environment and is continuously exposed to both endogenous and environmental factors that can cause damage and accelerate skin aging. Oxidative stress from free radicals or reactive oxygen species (ROS) is considered to be a major contributor to the process of aging. The ROS are produced by normal chemical reactions in the body as well as by UV radiation, pollution, smoking, stress and other external factors. It has been demonstrated that, during ageing, ROS levels rise in the skin while the antioxidant defenses decline. Oxidative stress is involved in the damage of cellular constituents, such as DNA, cell membrane lipids and proteins. Therefore, antioxidants applied topically can play a key role in reducing the damage caused by free radicals in the skin.

Lipid peroxidation is a well-established mechanism of cellular injury in both plants and animals, and is used as an indicator of oxidative stress in cells and tissues. Lipid peroxides, derived from polyunsaturated fatty acids, are unstable and decompose to form a complex series of compounds. These include reactive carbonyl compounds, of which the most abundant is malondialdehyde (MDA). Measurement of MDA, therefore, is widely used as an indicator of lipid peroxidation (Esterbaur, 1991). Increased levels of lipid peroxidation products have been associated with a variety of chronic diseases in both humans and model systems. The thiobarbituric acid reactive substances (TBARS) assay is commonly used to measure MDA in biological samples. However, this reaction is relatively nonspecific as both free and protein-bound MDA can react.

The MDA-586 method is designed to assay free MDA or, after a hydrolysis step, total MDA (i.e., free and protein-bound Schiff base conjugates). The assay conditions serve to minimize interference from other lipid peroxidation products, such as 4-hydroxyalkenals.

UVB irradiation (280-320 nm) is well absorbed in various biological macromolecules such as proteins, lipids, and DNA causing damage directly by converting the irradiation energy to photochemical reactions. In addition, ROS (e.g. oxygen radicals and singlet oxygen) are produced, which can modify the cellular DNA and other cellular components, possibly leading to photo-carcinogenesis. The UVA component of solar radiation (320-400 nm) has also been shown to produce deleterious biological effects in which singlet oxygen plays a major role. This is of particular importance in tissue that is exposed to UVA irradiation, such as the skin and the eye.

Skin is frequently exposed to sunlight, and UVA exposure is thought to cause skin aging and skin cancer mainly through the action of singlet oxygen. Singlet oxygen mediates gene regulation via the transcription factor activator protein-2, activates stress-activated protein kinases, or induces in skin fibroblasts a pattern of mitogen-activated protein kinase as well as an induction of p38 and c-Jun-N-terminal kinase.

A limited number of molecules in tissue weakly absorb UVA irradiation. After UVA irradiation absorption, these molecules (endogenous photo-sensitizer) crossover to its long-lived triplet state that allows transferring energy to oxygen molecules. The transferred energy leads to an energetically excited oxygen molecule (singlet oxygen), which is highly reactive.

It is well known that t-butyl hydroperoxide (tBHP) mimics the lipid peroxidation on skin (human keratinocytes). tBHP is an organic peroxide used to induce free radical production in several biological systems. Red cells exposed to tBHP undergo lipid peroxidation, haemoglobin degradation and hexose monophosphate-shunt stimulation. Lipid peroxidation and haemoglobin degradation represent extremes of a spectrum of oxidative damage. tBHP induces cell death via apoptosis or necrosis. Erythrocyte haemolysis assay is one of the best cellular models to evaluate the anti-oxidative effect of a compound.

A dynamic and intact thylakoid membrane extract having both anti-oxidative and anti-inflammatory properties, and its use in combination with other anti-inflammatory compounds, have been described in International patent publication numbers WO 01/49305 and WO 01/04042, respectively. The anti-oxidative and anti-inflammatory properties of the thylakoid extract have been demonstrated in in vitro, ex vivo, in situ and in vivo studies. Specifically, the thylakoid extract has been shown to capture the noxious reactive oxygen species including singlet oxygen species, and to modulate pro- and anti-inflammatory cytokines toward attenuation of inflammation.

The use of thylakoid extracts as ROS scavengers, as photoprotectors, particularly against ultraviolet (UV) radiations, and as a solar screen because of its capacity to capture UV radiations and to dissipate the solar energy into heat, has also been described (WO 01/49305).

Furthermore, US 20070036877 discloses that, in vivo, topical applications of the thylakoid extract applied directly to the site of injury, have been shown to prevent or reduce the UV-induced skin damage in hairless mice.

There is a need for cosmetic and topical compositions containing an effective amount of a photosynthetic cell extract comprising a functional thylakoid system ("photosynthetic cell extract" or "extract") and having anti-wrinkle and anti-aging effects on a user's skin. There is also a need for cosmetic and topical compositions containing an effective amount of the photosynthetic cell extract to provide prolonged protection of the skin against ultraviolet A (UVA) and ultraviolet (UVB) damage.

SUMMARY OF THE INVENTION

The present invention provides a new use for a photosynthetic cell extract, that is, in a cosmetic composition comprising the photosynthetic cell extract in anti-aging and anti-oxidant applications for increasing the firmness and hydration of a user's skin and for protecting the user's skin against UVA and UVB damage.

The invention also relates to the cosmetic treatment of wrinkles by local or subcutaneous applications of a cosmetic composition containing the photosynthetic cell extract.

The invention also relates to the use of a photosynthetic cell extract against tissue and DNA damage induced by UVA or UVB radiation, and to a composition comprising the photosynthetic cell extract and an excipient for topical administration. The inventors have discovered a surprising synergism obtained by combining both the photosynthetic cell extract and a sunscreen to protect skin against UVA and UVB damage.

Furthermore, the inventors have discovered that the addition of a photosynthetic cell extract to a topical composition will prolong the composition's ability to protect the skin from UVA and UVB damage. A cream formulation containing the extract has been shown to protect against lipid peroxidation by UV irradiation and to protect against erythrocyte haemolysis, compared with formulations without the extract.

The photosynthetic cell extract comprises a unique natural antioxidant complex that has the ability to continuously capture and dissipate noxious energy generated by ROS. The extract is, therefore, capable of capturing ROS, neutralizing the ROS by dissipating the noxious energy generated by the ROS and the returning to its original state ready to repeat the cycle over and over again. It is this dynamism and capacity to regenerate that provides the extract with its unprecedented, long-lasting antioxidant protection.

The composition according to the invention can be prepared in and embodied in all pharmaceutical forms normally used for topical application. Furthermore, the composition may comprise the usual additives in the cosmetic and dermatological fields, such as fats, emulsifiers and co-emulsifiers, hydrophilic or lipophilic gelling agents, hydrophilic or lipophilic active ingredients, preservatives, anti-oxidants, solvents, fragrances, fillers, hydrophilic and lipophilic filters, dyestuffs, neutralizers, pro-penetrating agents and polymers.

The extract can be formulated in a liquid composition (a non-lyophilised extract), a lyophilized extract reconstituted in water, physiological saline or any other solution compatible with topical administration, in propylene glycol, or in a solid composition.

Engineered tissues were protected with sunscreen (SPF=7.5) alone, sunscreen plus 0.01% extract, or sunscreen plus 0.1% extract for 30 minutes. Control tissues were not protected. Protected and unprotected tissues were exposed or not to 750 kJ/m$^2$ of UVA. Immediately after irradiation, DNA was extracted from each sample treated with Nth and Fpg then fractionated by electrophoresis (C=Control, V=Vehicle, M=Molecular weight standard, SS=Sunscreen).

Figure 11:
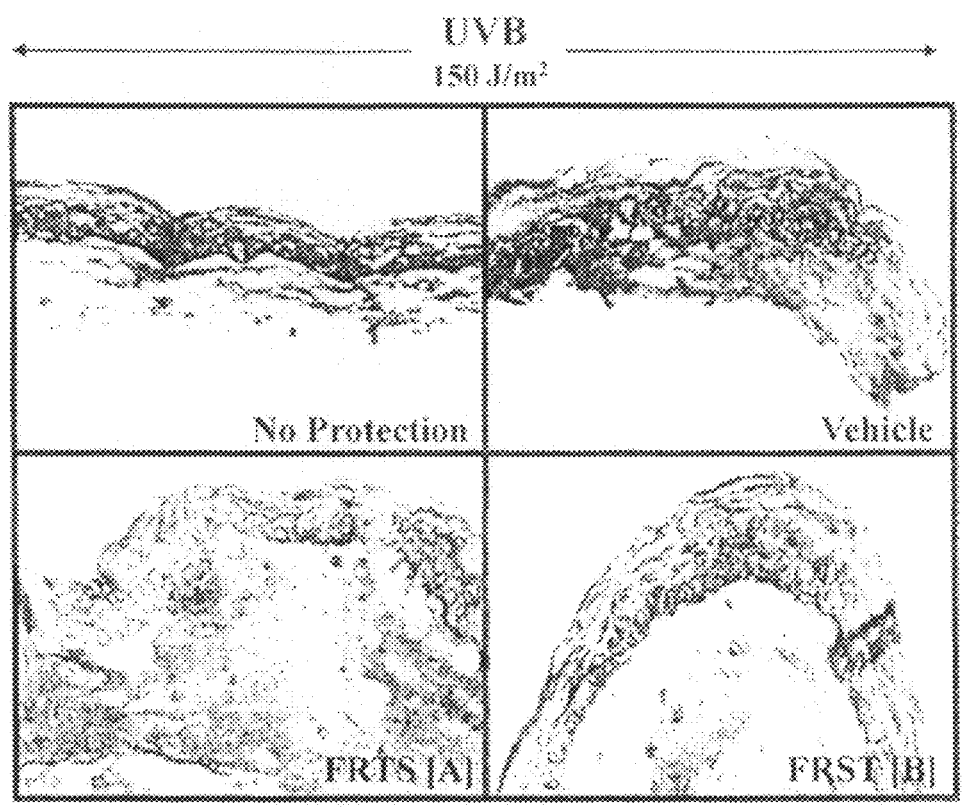

FIG. 11 illustrates the efficacy of the extract on repairing UVB-induced tissue damage. Engineered tissues were exposed to 150 J/m$^2$ of UVB. Immediately after irradiation, tissues were or not over layered with vehicle, or the extract at two concentrations: 0.01% and 0.1%. Three hours later, biopsies were collected and stained using Masson trichrome and observed using an optical microscope at 250× magnification.

Figure 12:
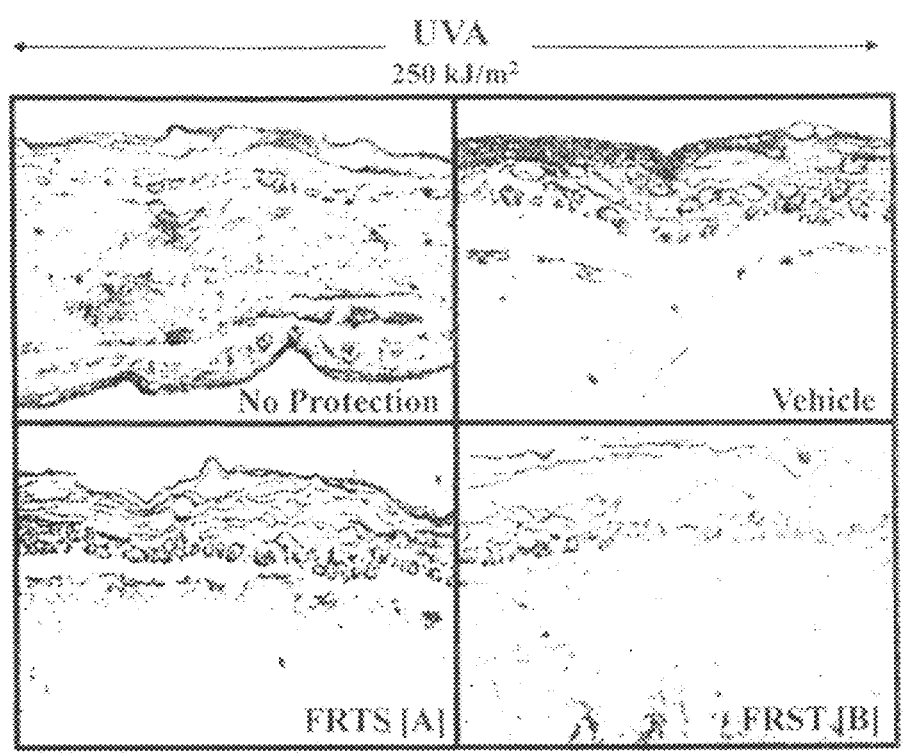

FIG. 12 illustrates the efficacy of the extract on repairing UVA-induced tissue damage. Engineered tissues were exposed to 250 kJ/m$^2$ of UVA. Immediately after irradiation, tissues were over layered or not with vehicle, or the extract at two concentrations: 0.01% and 0.1%. Three hours later, biopsies were collected and stained using Masson trichrome and observed using an optical microscope at 250× magnification.

Figure 13:
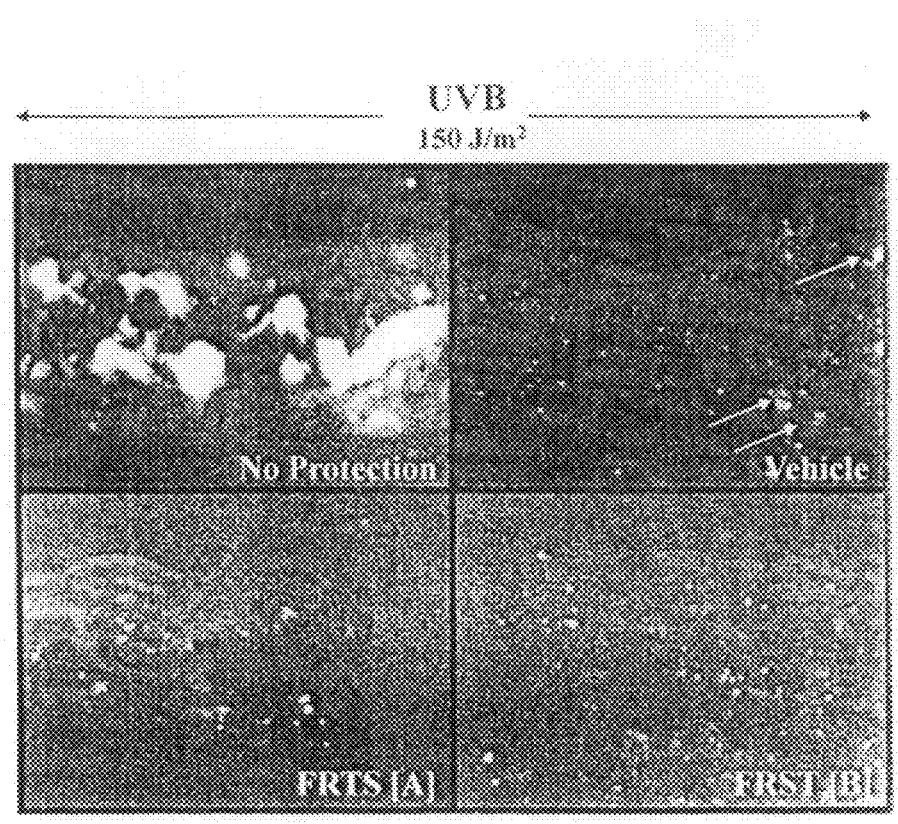

FIG. 13 illustrates the efficacy of the extract on repairing UVB-induced CPD formation. Engineered tissues were exposed to 150 J/m$^2$ of UVB. Immediately after irradiation, tissues were over layered or not with vehicle, or the extract at two concentrations: 0.01% and 0.1%. Three hours later, biopsies were collected and stained using anti-CPD monoclonal antibody and observed using a fluorescence microscope at 250× magnification.

Figure 14:
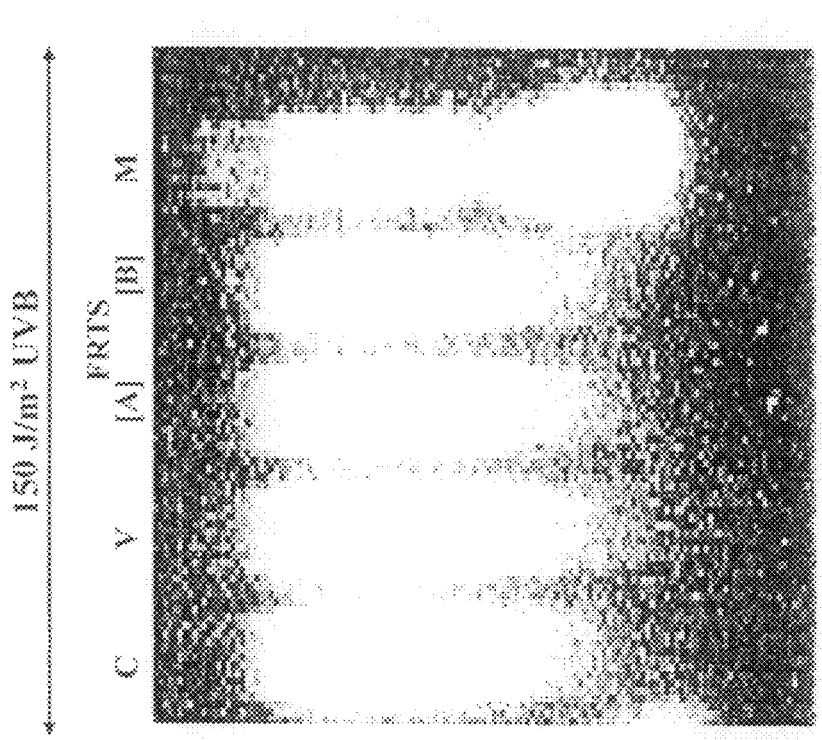

FIG. 14 illustrates the efficacy of the extract on repairing UVB-induced CPDs. Engineered tissues were exposed to 150 J/m$^2$ of UVB. Immediately after irradiation, tissues were over layered or not with vehicle, or the extract at two concentrations: 0.01% and 0.1%. Three hours later, DNA was extracted from each sample, treated with T4endo-V and fractionated by electrophoresis (C=Control, V=Vehicle, M=Molecular weight standard).

Figure 15:
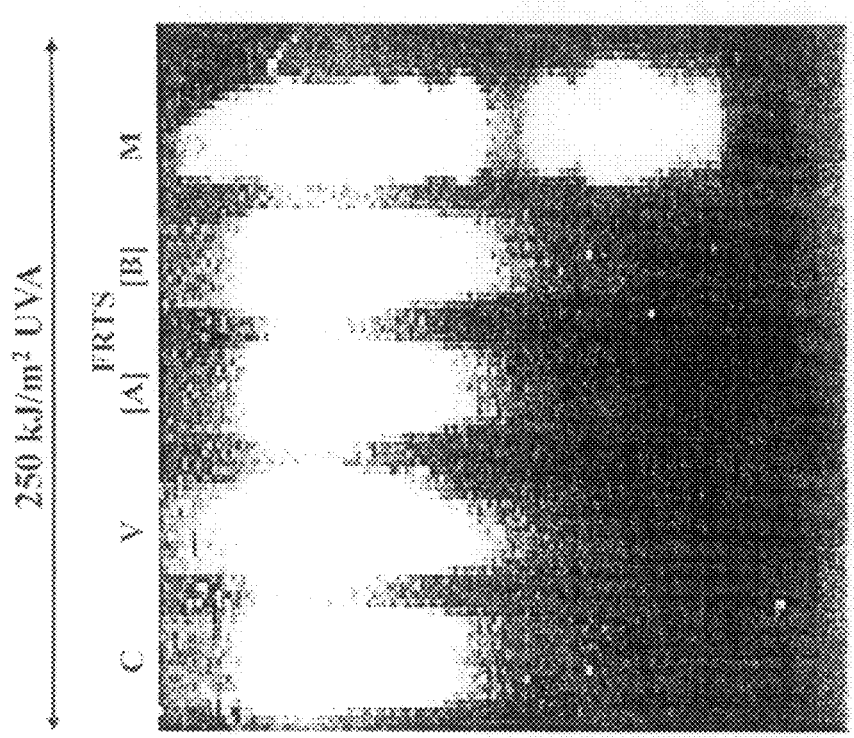

FIG. 15 illustrates the efficacy of the extract on repairing UVA-induced photo-oxidative damage. Engineered tissues were exposed to 250 kJ/m$^2$ of UVA. Immediately after irradiation, tissues were over layered or not with vehicle, or the extract at two concentrations: 0.01% and 0.1%. Three hours later, DNA was extracted from each sample treated with Nth and Fpg then fractionated by electrophoresis (C=Control, V=Vehicle, M=Molecular weight standard).

Figure 16:
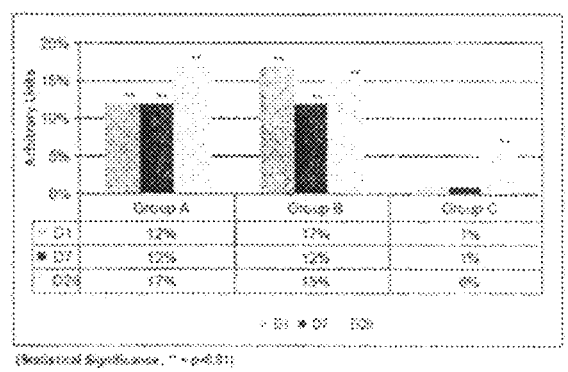

FIG. 16 illustrates the percent improvement in hydration at Day 1, Day 7 and Day 28 compared to Day 0 as measured by Corneometer®.

Figure 17:
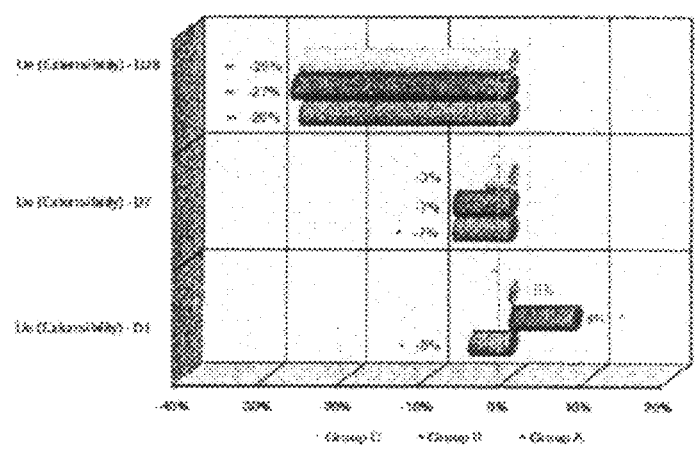

FIG. 17 illustrates the evolution of Ue (extensibility) at Day 1, Day 7 and Day 28 compared to Day 0.

Figure 18:
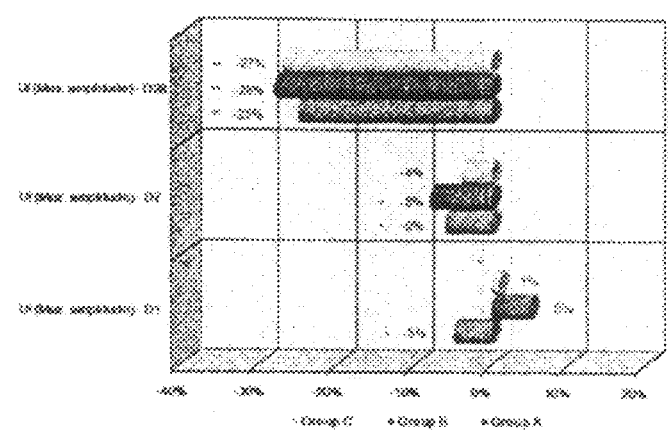

FIG. 18 illustrates the evolution of Uf (Max. amplitude) at Day 1, Day 7 and Day 28 compared to Day 0.

Figure 19:
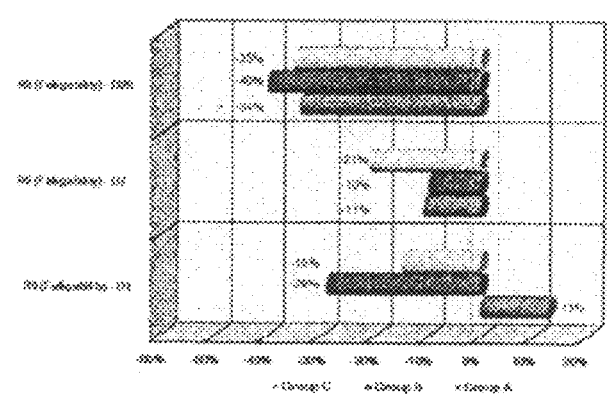

FIG. 19 illustrates the evolution of R9 (fatigability) at Day 1, Day 7 and Day 28 compared to Day 0.

Figure 20:
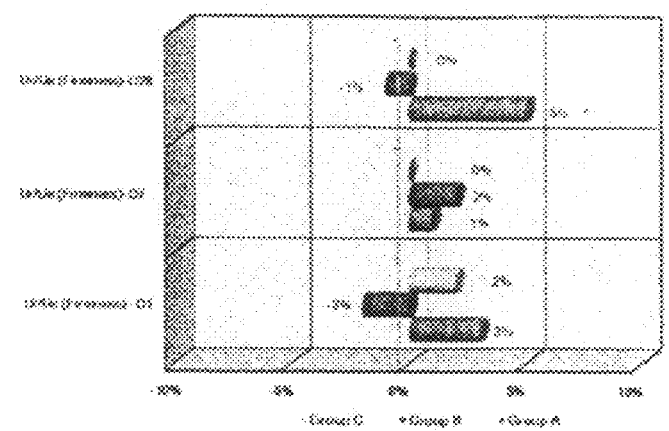

FIG. 20 illustrates the evolution of Ur/Ue (firmness) at Day 1, Day 7 and Day 28 compared to Day 0.

Figure 21:
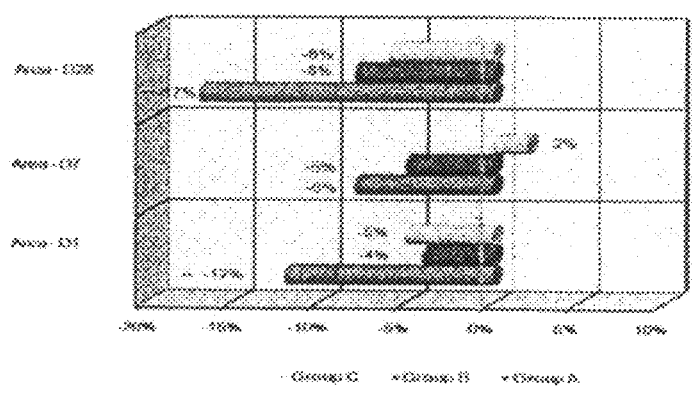

FIG. 21 illustrates the area of wrinkles at Day 1, Day 7 and Day 28 compared to Day 0.

Figure 22:
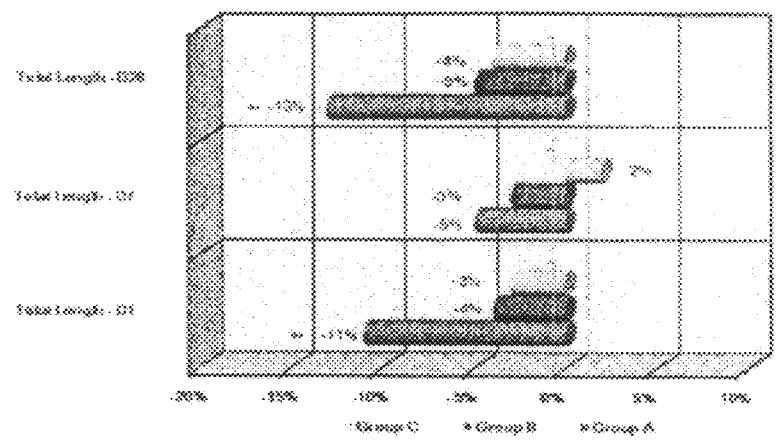

FIG. 22 illustrates the evolution of the total length of wrinkles at Day 1, Day 7 and Day 28 compared to Day 0.

Figure 23:
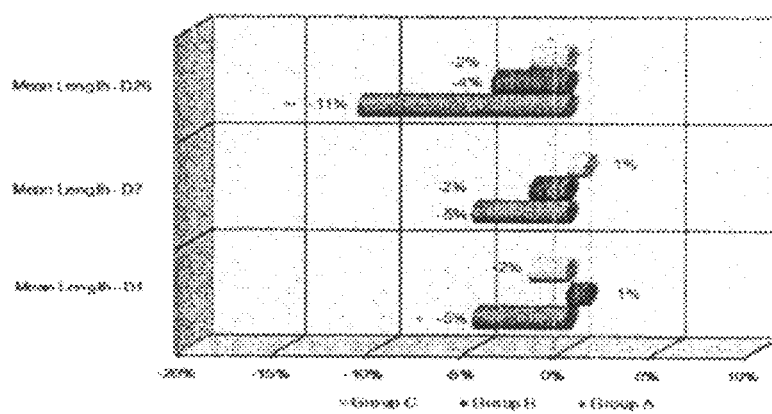

FIG. 23 illustrates the evolution of the mean length of the wrinkles at Day 1, Day 7 and Day 28 compared to Day 0.

Figure 24:
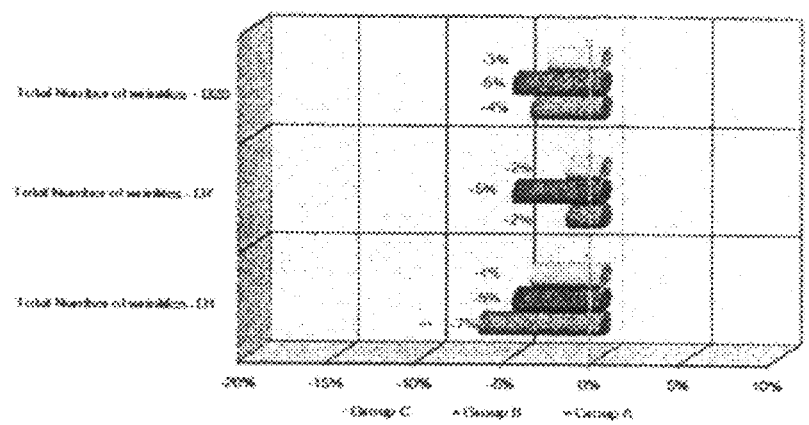

FIG. 24 illustrates the total number of wrinkles at Day 1, Day 7 and Day 28 compared with Day 0.

Figure 25:
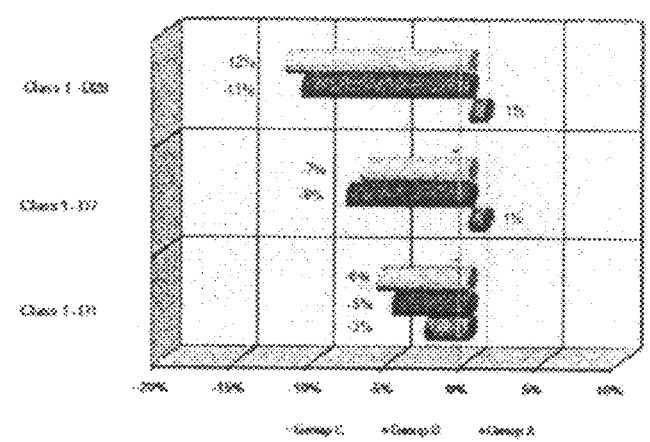

FIG. 25 illustrates the evolution of the number of wrinkles in Class 1 at Day 1, Day 7 and Day 28 compared to Day 0.

Figure 26:
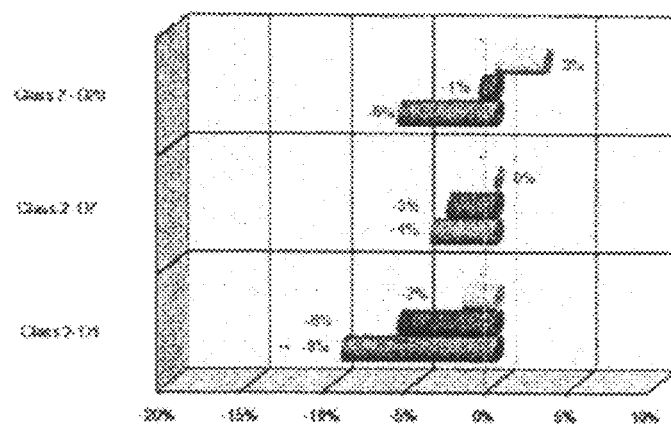

FIG. 26 illustrates the evolution of the number of wrinkles in Class 2 at Day 1, Day 7 and Day 28 compared to Day 0.

Figure 27:
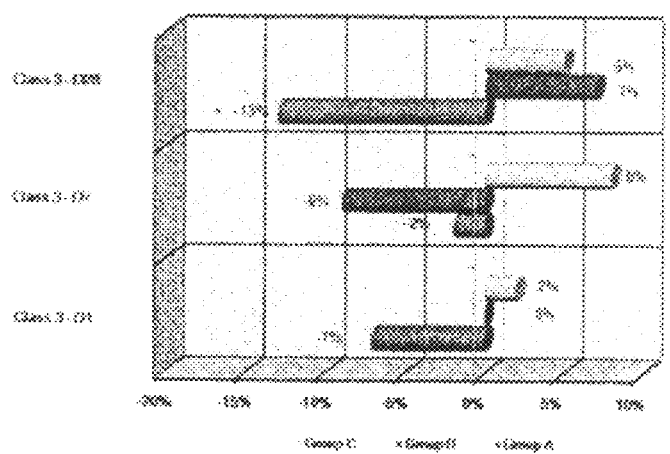

FIG. 27 illustrates the evolution of the number of wrinkles in Class 3 at Day 1, Day 7 and Day 28 compared to Day 0.

Figure 28:
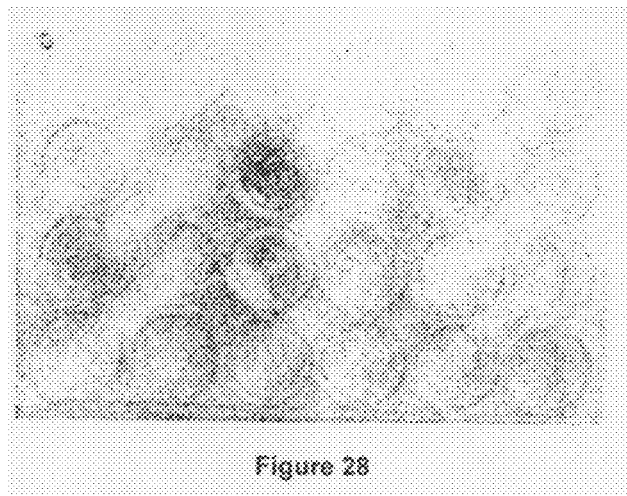

FIG. 28: illustrates irradiation wells showing fatty acids and cream formulation mixed (1:1) and irradiated for 10 minutes.

Figure 29A:
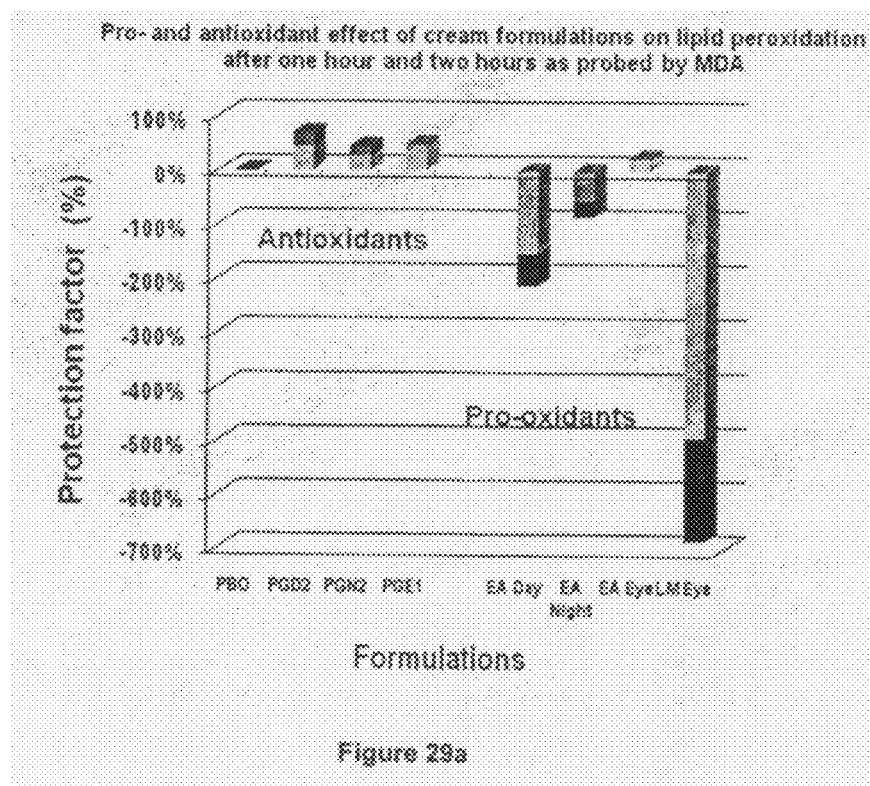

FIG. 29a: illustrates the protection factor of cream formulations against lipid peroxidation caused by UV irradiation (10 minutes); after 1 hour incubation (green and blue) and 2 hours of incubation (dark green and red) at 45° C. (Abbreviations: PBO, placebo cream; PGD2, PurGenesis day (0.01% extract); PGN2, PurGenesis night (0.015% extract); PGE1, PurGenesis eye (0.02% extract); EA, Elisabeth Arden Prevage; LM, La Mer.) Final concentration: fatty acids 10% (v/v); cream formulations: 10% (p/v).

Figure 29B:
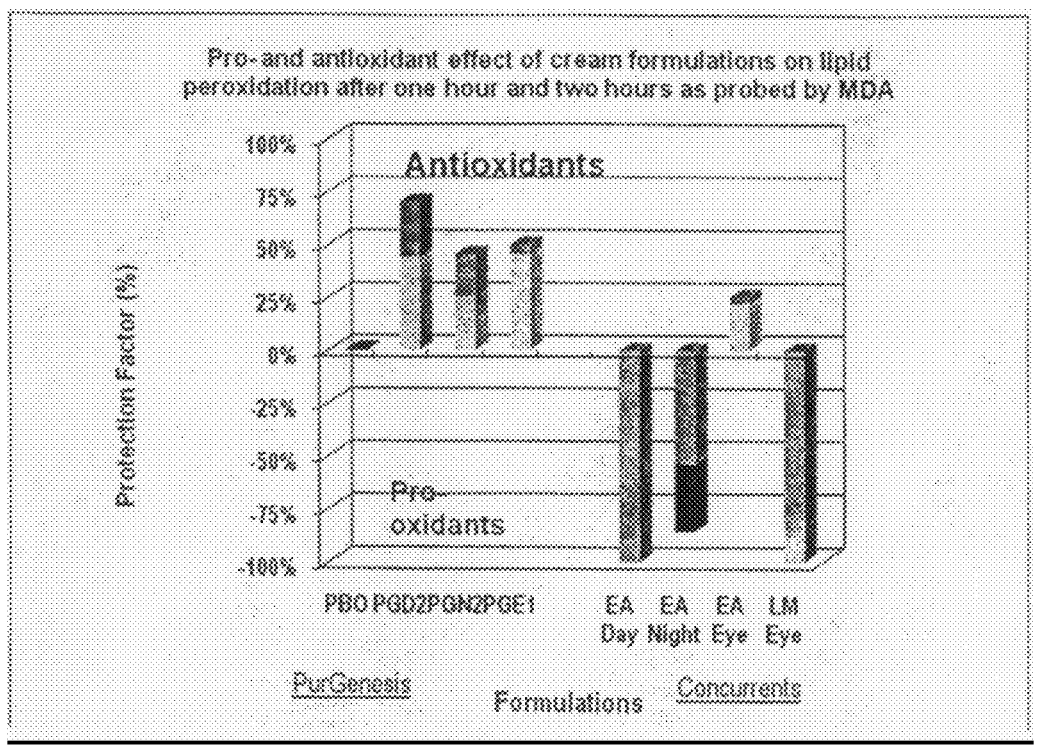

FIG. 29b: illustrates the protection factor of cream formulations against lipid peroxidation caused by UV irradiation (10 minutes); after 1 hour incubation (green and blue) and 2 hours of incubation (dark green and red) at 45° C. The pro-oxidant effect is restricted at 100%. (Abbreviations: PBO, placebo cream; PGD2, PurGenesis day (0.01% extract); PGN2, PurGenesis night (0.015% extract); PGE1, PurGenesis eye (0.02% extract); EA, Elisabeth Arden Prevage; LM, La Mer.) Final concentration: fatty acids 10% (v/v); cream formulations 10% (p/v)

Figure 29C:
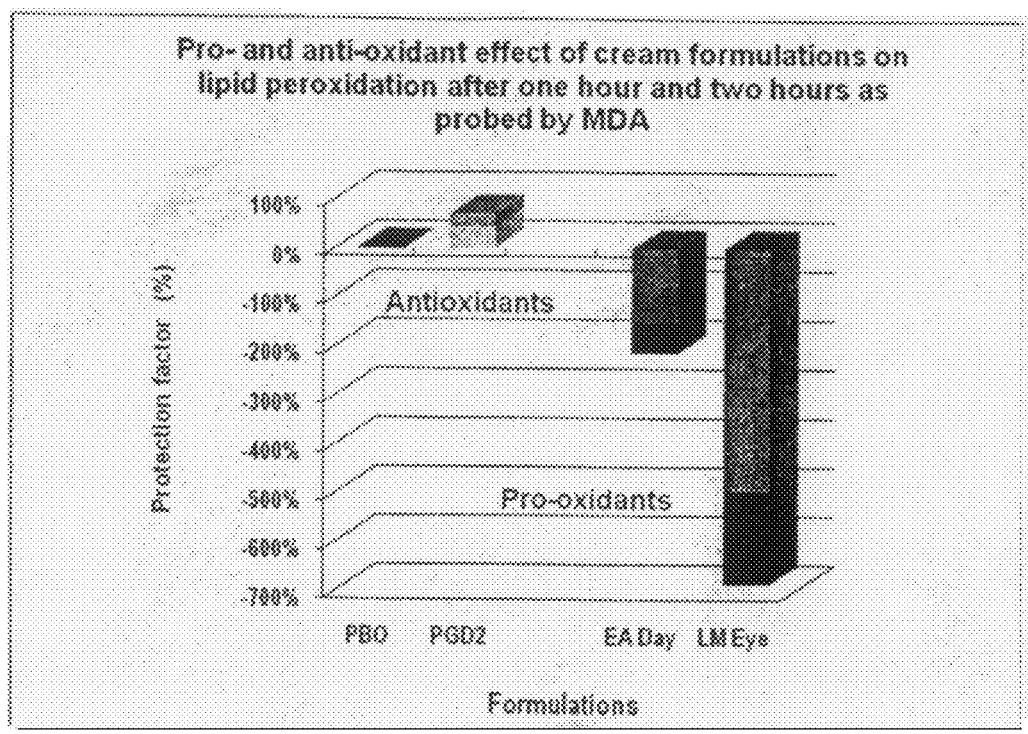

FIG. 29c: illustrates the protection factor of cream formulations against lipid peroxidation caused by UV irradiation (10 minutes); after 1 hour incubation (green and blue) and 2 hours of incubation (dark green and red) at 45° C. (Abbreviations: PBO, placebo cream; PGD2, PurGenesis day (0.01% extract); EA, Elisabeth Arden Prevage; LM, La Mer.) Final concentration: fatty acids 10% (v/v); cream formulations 10% (p/v).

Figure 29D:
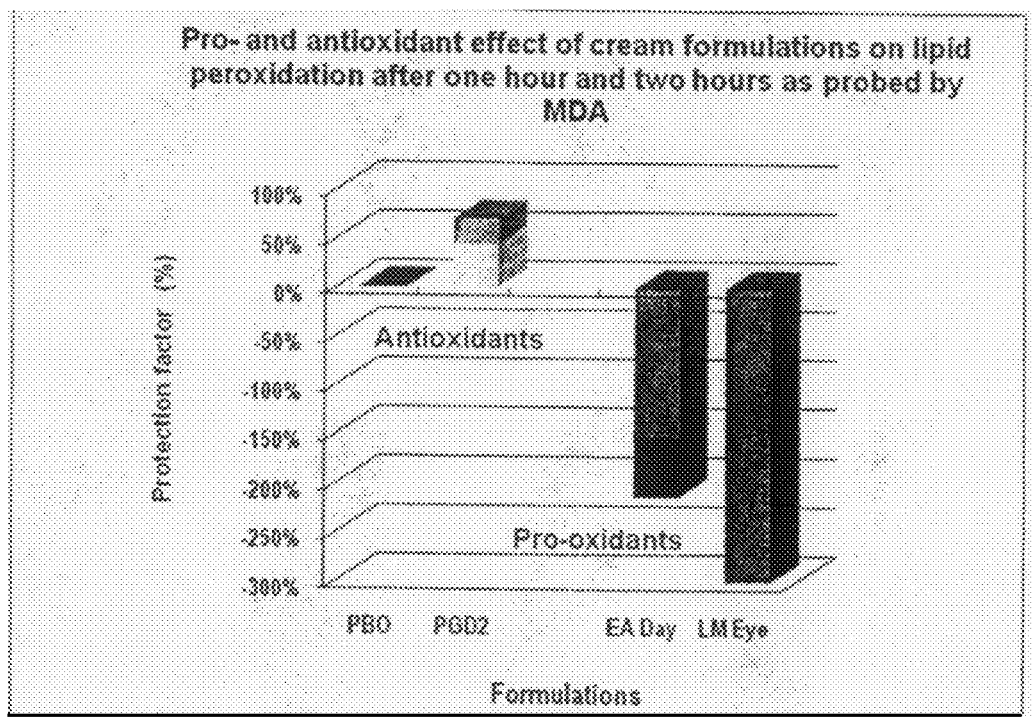

FIG. 29d: illustrates the protection factor of cream formulations against lipid peroxidation caused by UV irradiation (10 minutes); after 1 hour incubation (green and blue) and 2 hours of incubation (dark green and red) at 45° C. The pro-oxidant effect is cut off at 300%. PBO, placebo cream; PGD2, PurGenesis day (0.01% extract); PGN2, PurGenesis night (0.015% extract); PGE1, PurGenesis eye (0.02% extract); EA, Elisabeth Arden Prevage; LM, La Mer. Final concentration: fatty acids, 10% (v/v); cream formulations 10% (p/v).

Figure 29E:
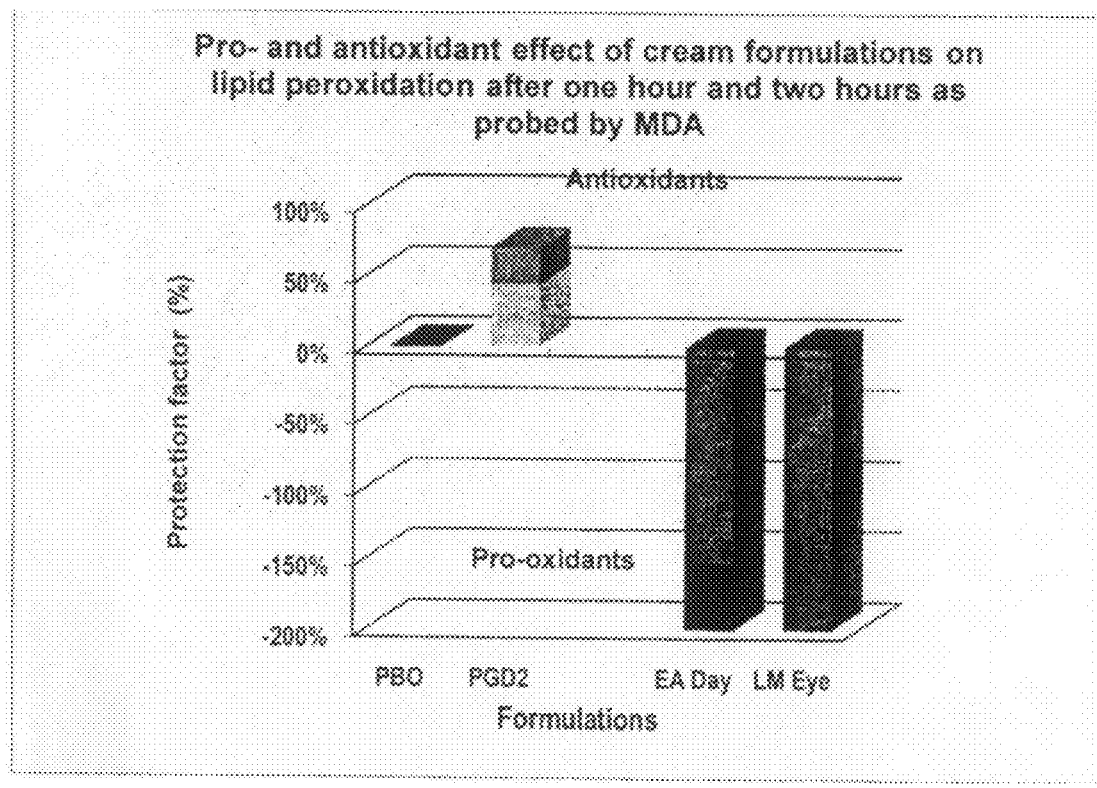

FIG. 29e: illustrates the protection factor of cream formulations against lipid peroxidation caused by UV irradiation (10 minutes); after 1 hour incubation (green and blue) and 2 hours of incubation (dark green and red) at 45° C. The pro-oxidant effect is cut off at 200%. PBO, placebo cream; PGD2, PurGenesis day (0.01% extract); PGN2, PurGenesis night (0.015% extract); PGE1, PurGenesis eye (0.02% extract); EA, Elisabeth Arden Prevage; LM, La Mer. Final concentration: fatty acids, 10% (v/v); cream formulations 10% (p/v).

Figure 30:
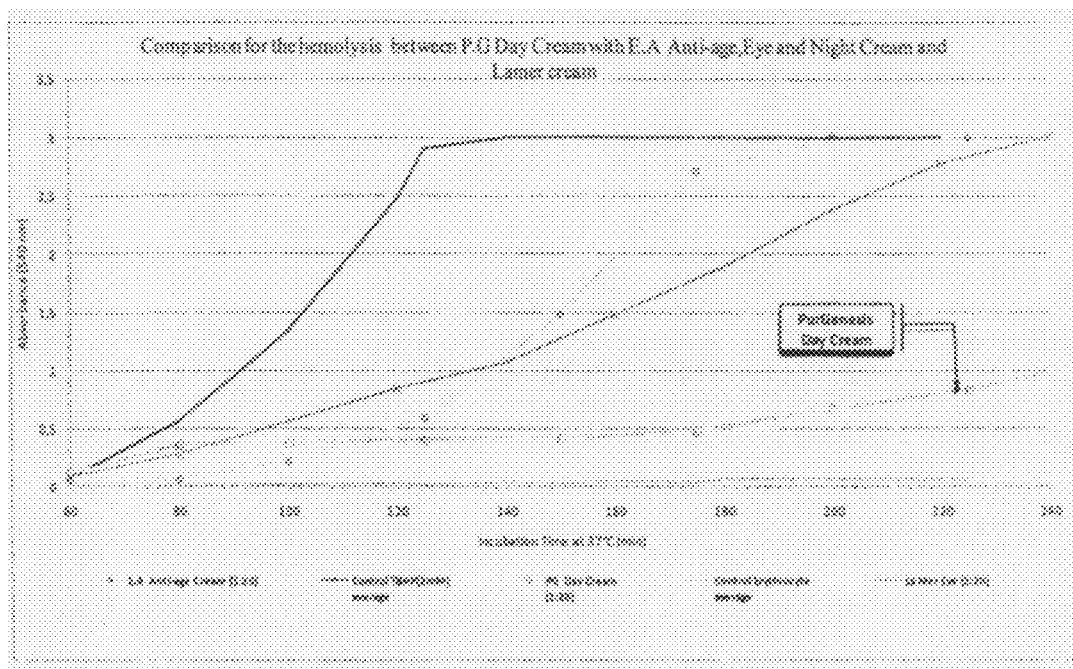

FIG. 30: illustrates the haemolysis of bovine erythrocytes caused by tBHP (2 mM) with and without cosmetic formulations.

Figure 31:
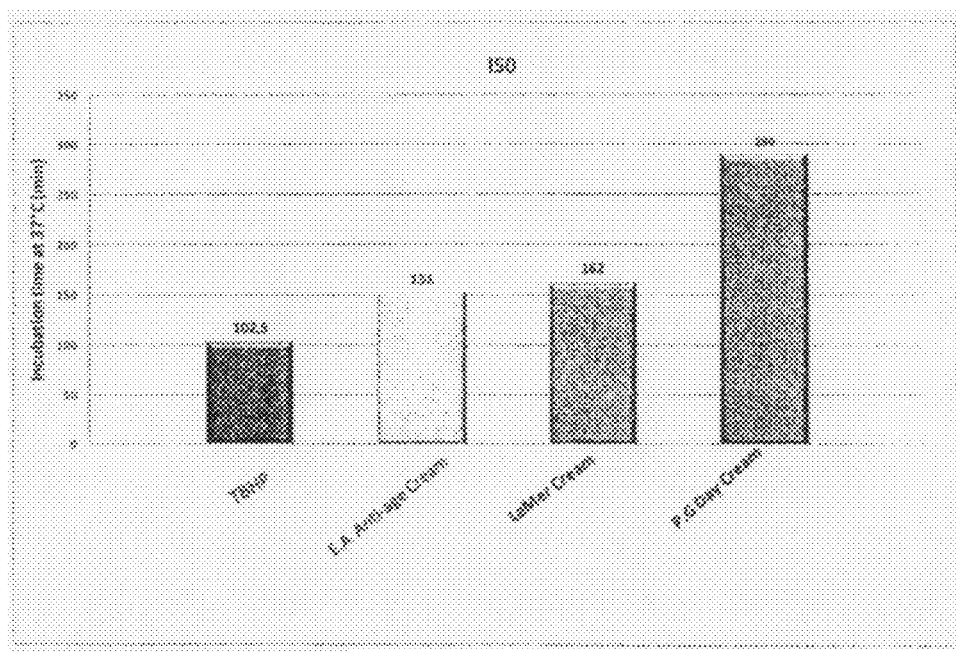

FIG. 31: illustrates 150 haemolysis; relative incubation time to provoke 50% of cellular damage.

Figure 32:
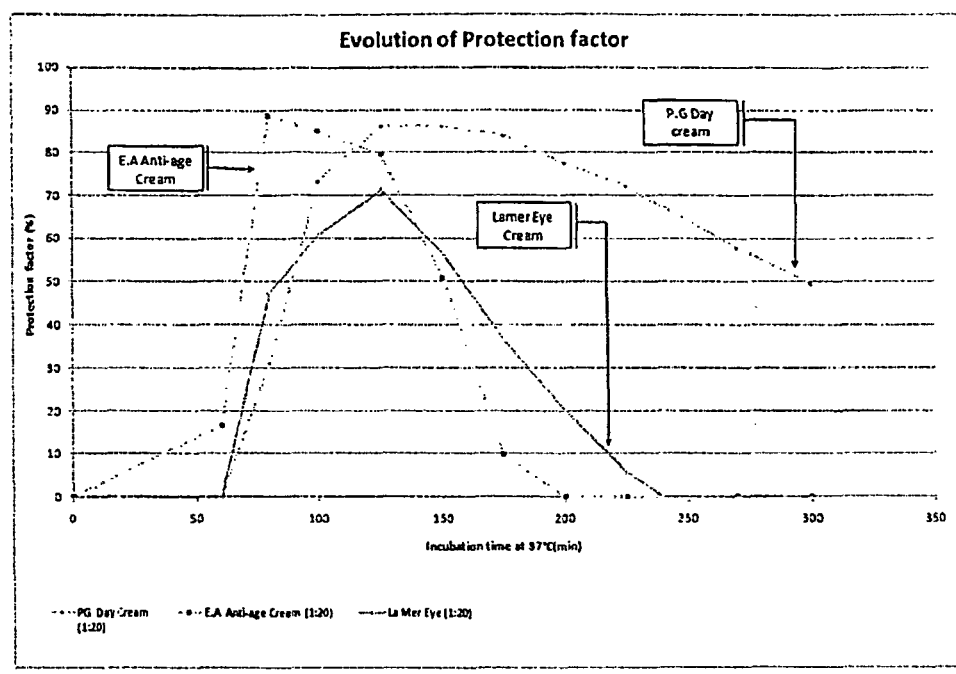

FIG. 32: illustrates the relative protection factor of three cosmetic formulations (0.01%, 0.015% and 0.02% extract concentration).

Figure 33:
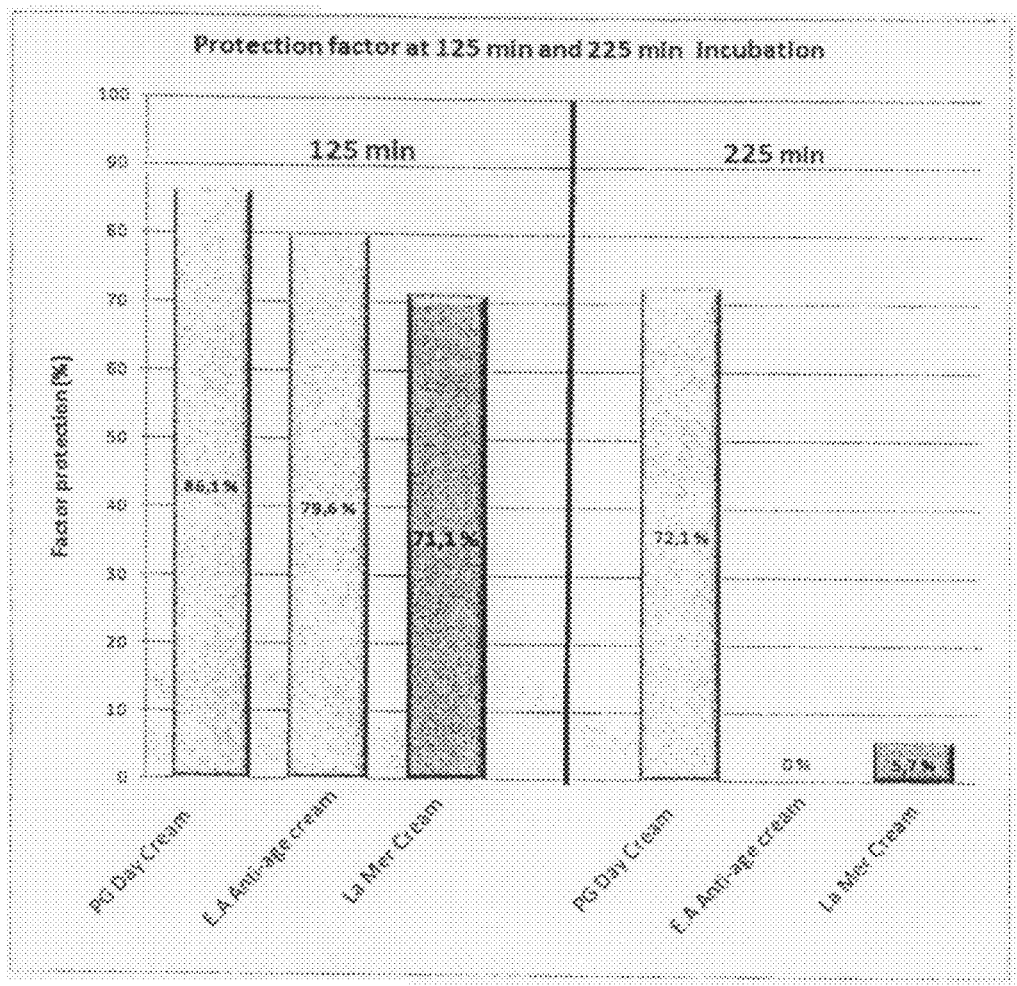

FIG. 33: illustrates the comparison of the protection factor against bovine erythrocyte haemolysis for the three cosmetic formulations (0.01%, 0.015% and 0.02% extract concentration), after 125 and 225 minutes of incubation.

Figure 34:
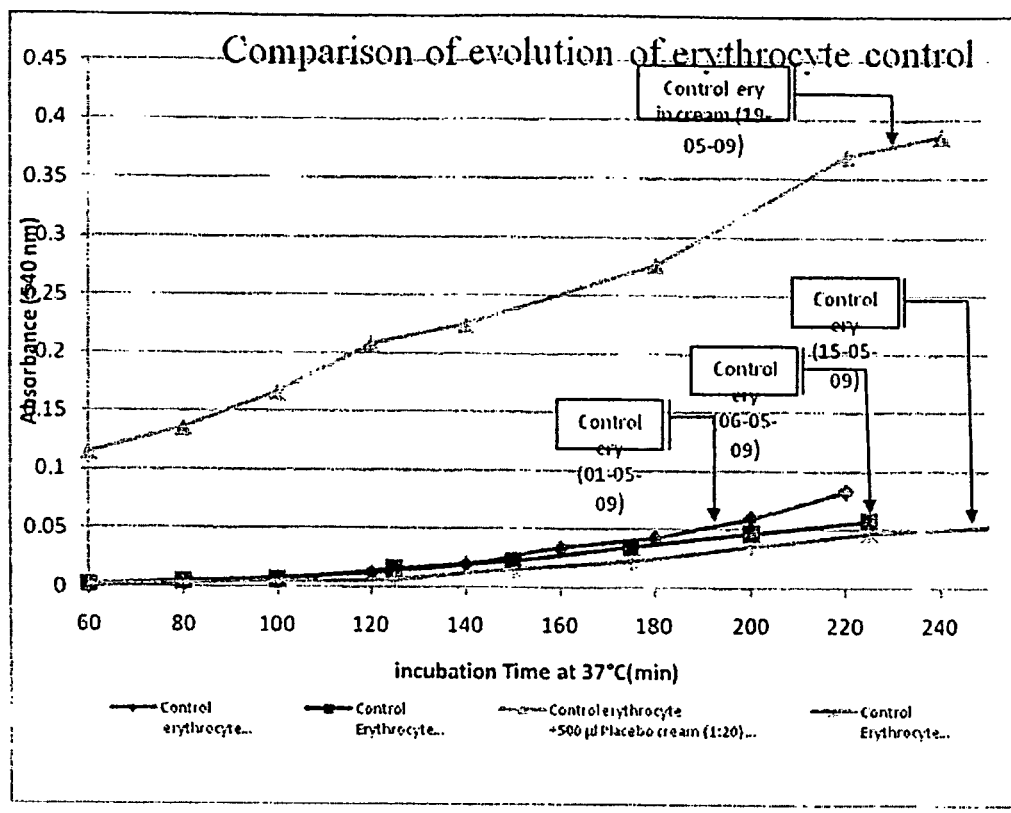

FIG. 34: illustrates the control (without tBHP): Triplicate plus control in cream.

DETAILED DESCRIPTION

Use of Extract to Protect Skin Against UVA and UVB Damage

In accordance with the present invention, two topical compositions were developed: one comprising 0.01% of the extract and one comprising 0.1% of the extract.

Using artificial sources of UVA and UVB radiation, and topical compositions comprising the two extract concentrations, and a topical composition which did not contain any extract, the inventors evaluated morphological changes, CPD formation, and DNA damage in engineered human skin (EHS) when compared with unprotected (control) EHS.

The morphological analysis indicated that the extract provides protection of EHS against UVA structural damage.

The inventors further discovered that, when added to commercial sunscreen lotion, the photosynthetic cell extract decreased UVA/UVB-induced DNA damage in the EHS.

The compositions containing the two concentrations of the extract demonstrated obvious improvements in the repair of EHS structural and DNA damage induced by both UVB and UVA. The inventors discovered, therefore, that the extract promotes the repair of UVA-induced DNA photo-oxidative damage.

Moreover, it was shown that the addition of a low concentration of the extract (0.01%) to conventional sunscreen demonstrated a surprisingly significant increase in the protection against UV induced DNA damage.

Efficacy of the Extract Against UVB-Induced EHS Tissue Damage

Figure 1:
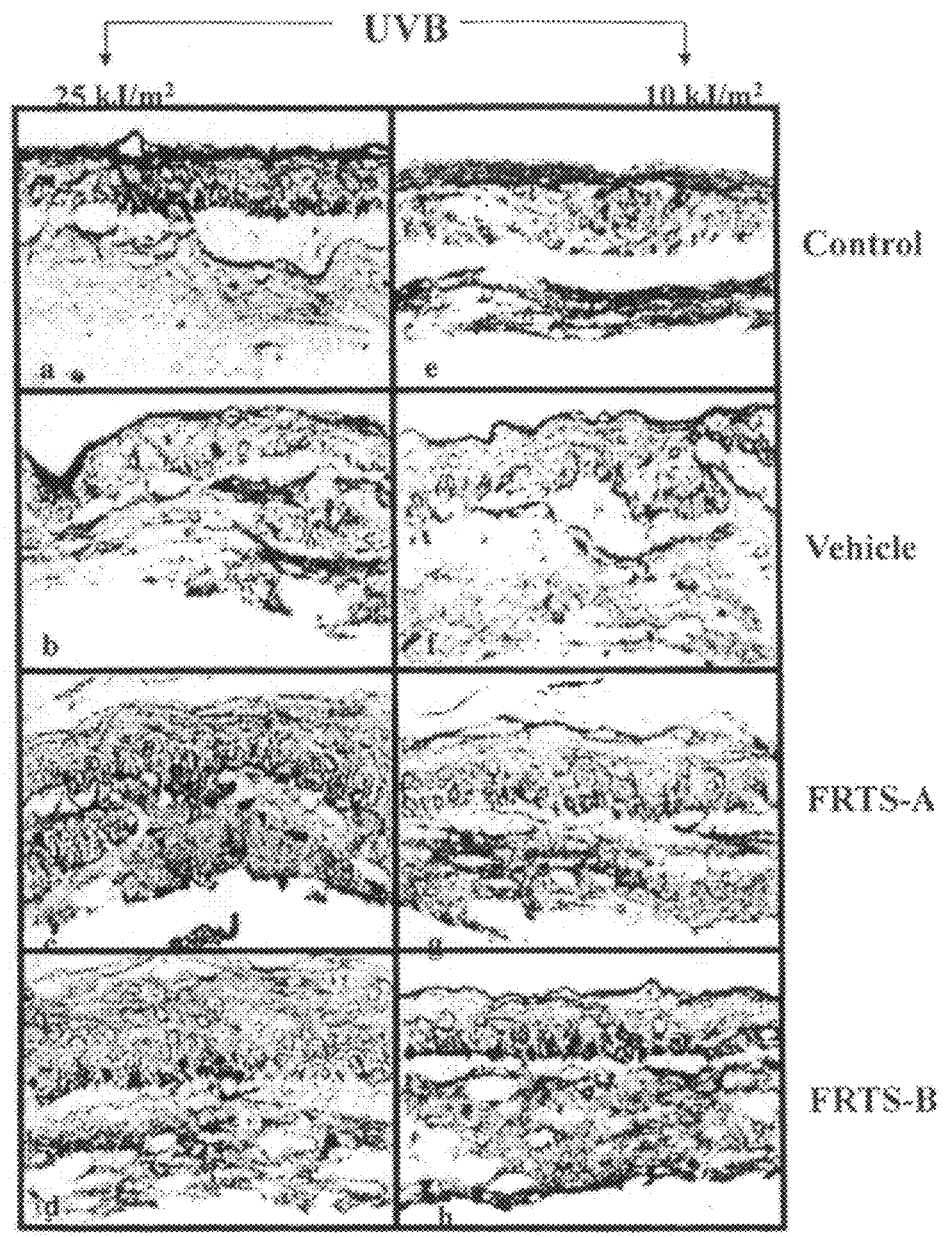
FIG. 1 illustrates the efficacy of the extract against UVB-induced tissue damage. Damage was observed following exposure to two levels of UVB exposure (10 and 25 $kJ/m^2$) in untreated tissue (control), tissue treated with an extract-free composition (vehicle), and tissue treated with compositions comprising 0.1% (A) and 0.01% (B) of the extract.

The inventors compared EHS treated with topical compositions comprising 0.1% extract, 0.01% extract, and no extract (vehicle) with untreated EHS (control). The EHS was exposed to UVB at 10 and 25 $kJ/m^2$. As shown in FIG. 1, the different strata (germinativum, granulosum, spinosum and corneum) of EHS exposed to UVB were less distinguishable from each other compared to UVB-unexposed tissues. As the UVB dose was increased from 10 to 25 $kJ/m^2$, there was an increase in epidermal disorganization as determined by the thickening of the stratum corneum and reduction in the number of epidermal cell layers (FIGS. 1a and 1e). Morphologically differentiated keratinocytes (large cells with faint nuclei, large cytoplasm, and the presence of vacuoles) were also induced in these irradiated tissues. Comparable changes were observed in vehicle-treated EHS (FIGS. 1b and 1f). Extract-protected EHS showed slight reduction of tissue or cellular damage (FIGS. 1c, 1d, 1g and 1h). However, the different epidermal layers of both the protected and unprotected EHS remained visible.

These histological analyses suggest that the compositions containing the extract at both concentrations (0.01% and 0.1%) did not act as an efficient tissue structure protector against elevated doses of UVB irradiation (10-25 $kJ/m^2$).

Efficacy of the Extract Against UVA-Induced EHS Tissue Damage

Figure 2:
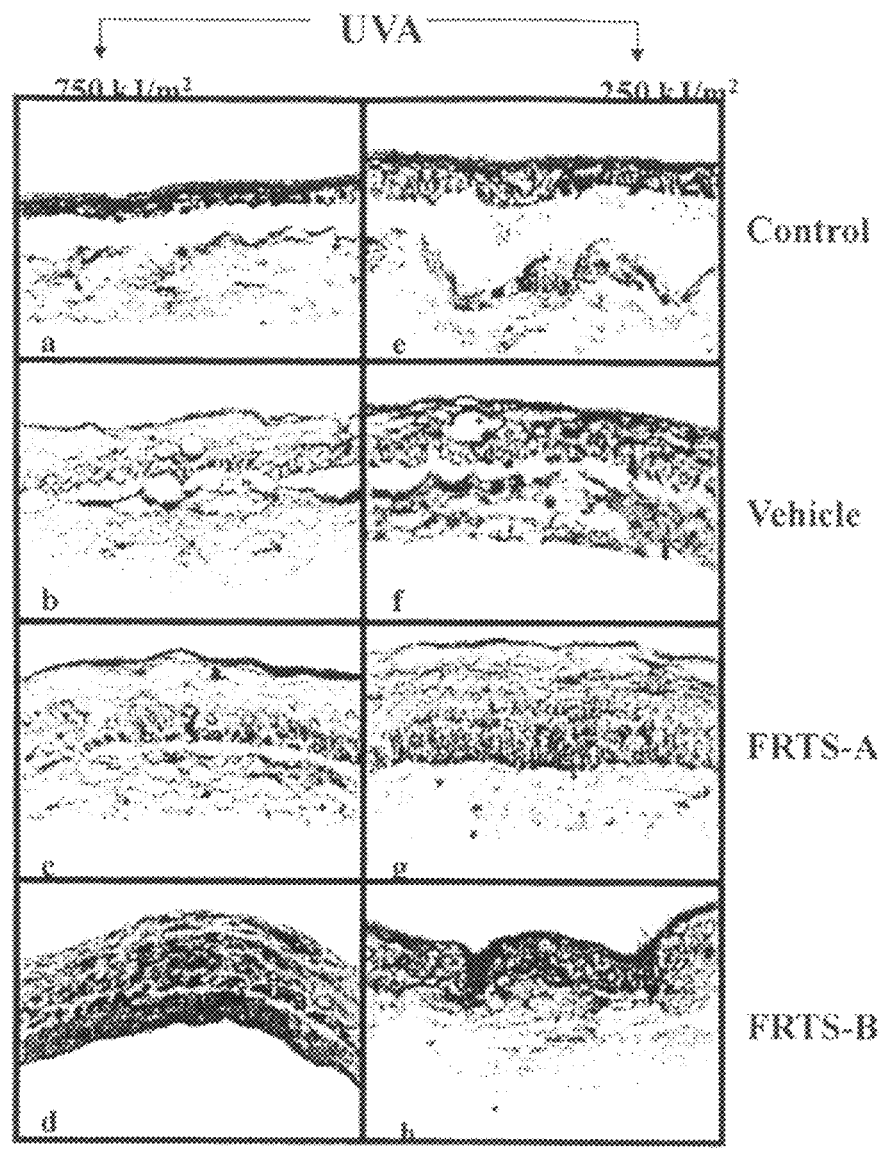
FIG. 2 illustrates the efficacy of the extract against UVA-induced tissue damage. Damage was observed following exposure to two levels of UVA exposure (250 and 750 $kJ/m^2$) in untreated tissue (control), tissue treated with an extract-free composition (vehicle), and tissue treated with compositions comprising 0.1% (A) and 0.01% (B) of the extract.

The inventors compared EHS treated with topical compositions comprising 0.1% extract, 0.01% extract, and no extract (vehicle) with untreated EHS (control). The EHS was exposed to UVA at 750 and 250 $kJ/m^2$. As shown in FIG. 2, the different strata (germinativum, granulosum, spinosum and corneum) of EHS exposed to UVA were completely disorganized and were less distinguishable from each other compared to UVA-unexposed tissues. The tissue disorganization, as determined by the thickening of the stratum corneum and reduction in the number of epidermal cell layers (FIGS. 1a and 1e), was higher following exposure to 750 $kJ/m^2$ compared to 250 $kJ/m^2$. Morphologically, the inventors were unable to identify cells in the UVA irradiated epidermis. Comparable changes were observed in vehicle-treated EHS (FIGS. 1d and 1f) but to a lesser extent. Conversely, extract-protected EHS showed significant reduction of tissue or cellular damage induced by UVA. The different epidermal layers of the protected EHS remained visible (FIGS. 1c, 1d, 1g, and 1h) for both extract concentrations (0.01% and 0.1%). These histological analyses revealed that the compositions comprising the extract protected tissue structure against UVA damage.

Efficacy of the Extract Against UVB-Induced EHS DNA Damage.

Figure 3:
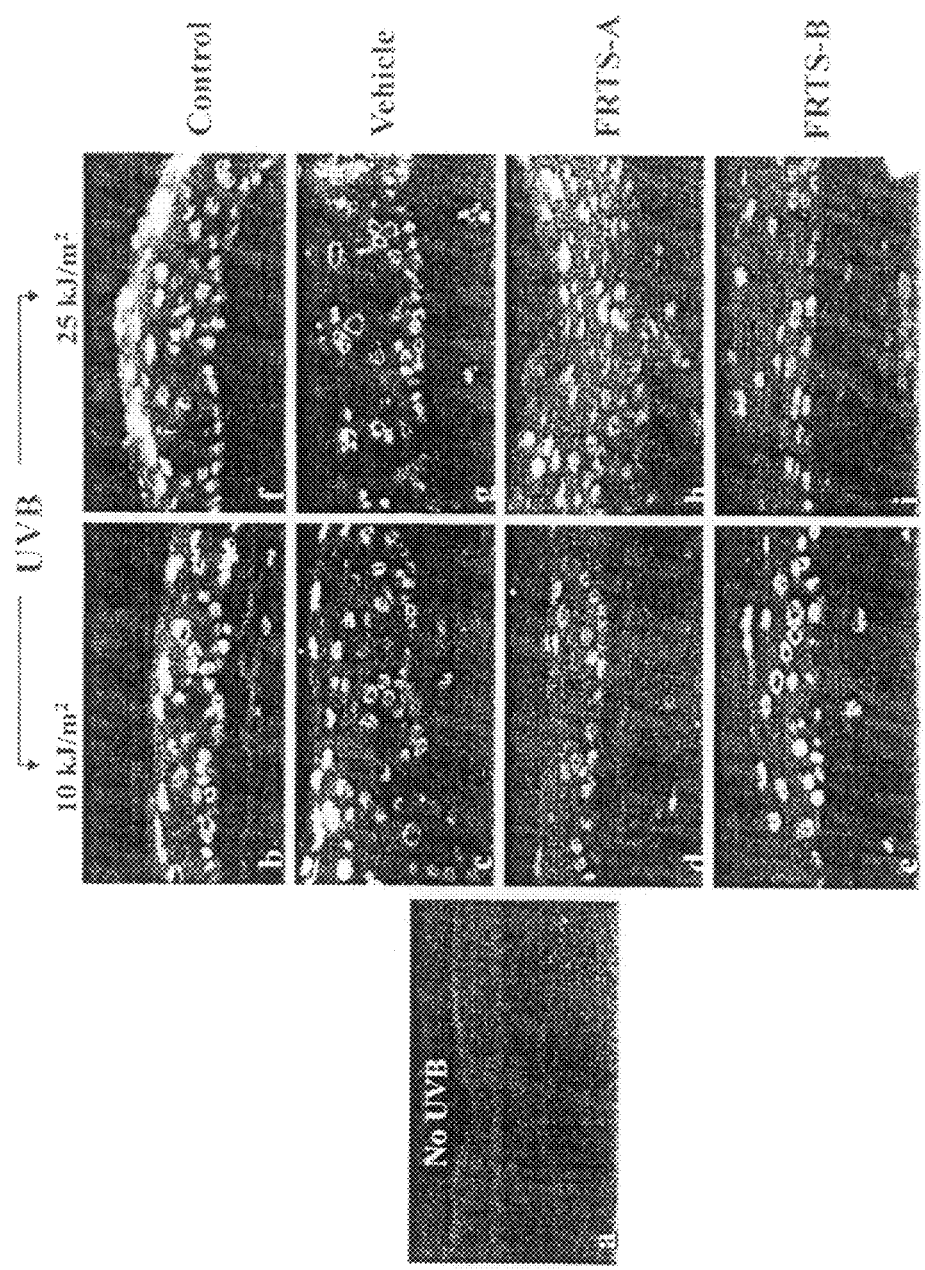
FIG. 3 illustrates the efficacy of the extract against UVB-induced cyclobutane pyrimidine dimer (CPD) formation.

Using immunofluorescence micrography, the inventors evaluated the effect of the extract on CPD formation and distribution following UVB exposure. As shown in FIG. 3, two doses of UVB, 10 $kJ/m^2$ and 25 $kJ/m^2$, induced CPDs in the majority of the epidermal cells in the unprotected (control) EHS (FIGS. 3b and 3f). CPD-positive nuclei were distributed throughout the full thickness of the epidermis, with a greater proportion of CPD-stained nuclei in the basal layer. The application of the vehicle-treatment did not prevent the appearance of CPD-positive cells (FIGS. 3c and 3g). While the number of CPD-stained cells is slightly higher in the unprotected tissue (FIGS. 3b, 3f, 3c and 3g) compared to extract-protected (FIGS. 3d, 3h, 3e and 3i) tissue, the prevention of the formation of CPD was not significant.

Figure 4:
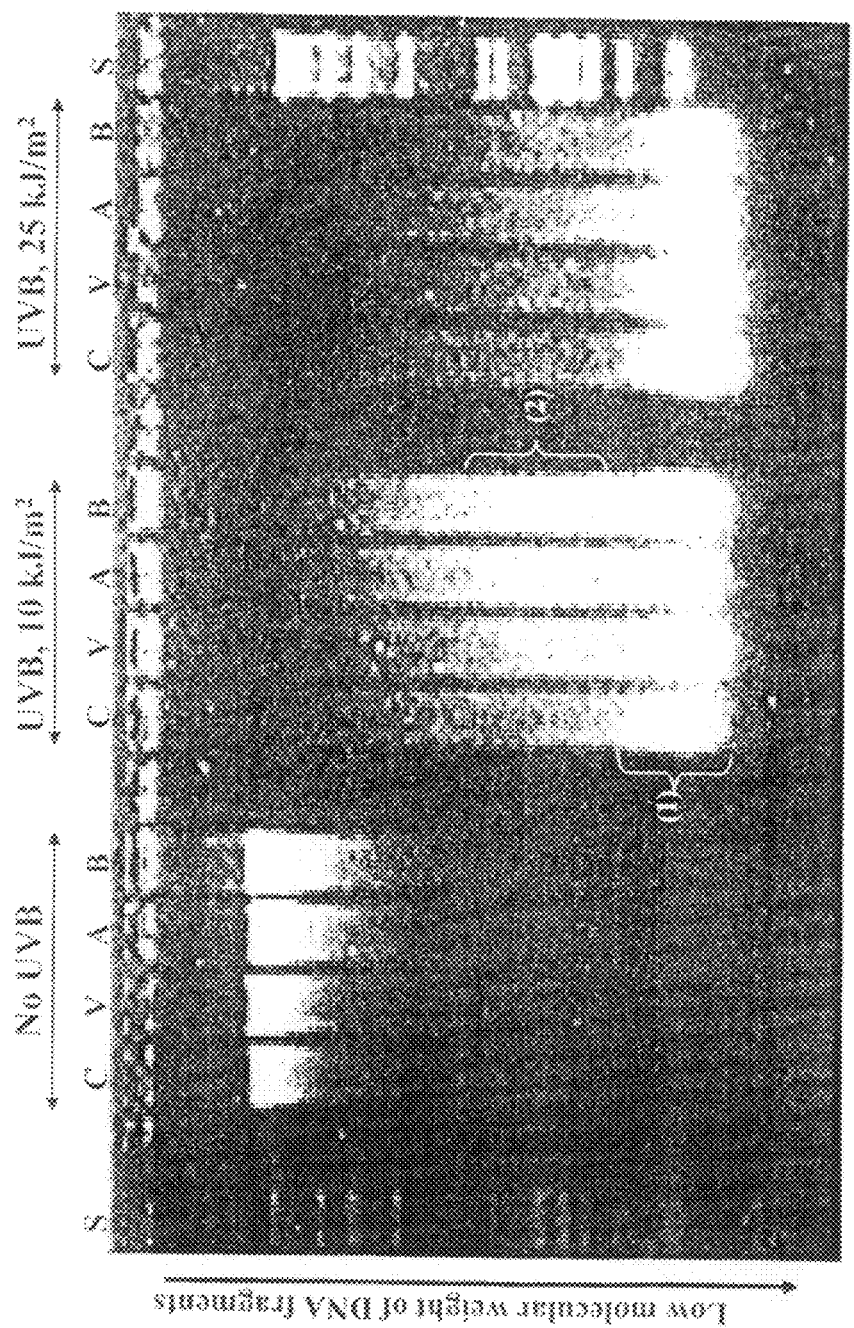
FIG. 4 illustrates the evaluation of CPD frequency following extract treatment then UVB irradiation where (1) indicates the damage induced by UVB as judged by the low molecular weight of DNA fragments and (2) indicates the protection offered by the extract, as judged by the presence of DNA at higher molecular weight than shown in unprotected tissue.

The inventors also measured the frequency of CPDs using neutral glyoxal gel electrophoresis. The effects of UVB on the global frequency of CPDs in the epidermis of EHS are shown in FIG. 4, where low molecular weight DNA fragments indicate UVB-induced damage. Analysis of DNA fragment mobility distribution showed that much smaller DNA fragments were present in all treated tissues. After exposure to 10 $kJ/m^2$ of UVB, as revealed by the DNA smears, the compositions comprising the two concentrations of extract slightly prevented DNA damage during irradiation although no protection by the extract was observed at 25 $kJ/m^2$ irradiation.

These results indicate that the extract at both concentrations (0.01% and 0.1%) did not significantly protect EHS cells against DNA damage induced by UVB irradiation at 10 and 25 $kJ/m^2$.

Efficacy of the Extract Against UVA-Induced EHS Cell Damage.

Figure 5:
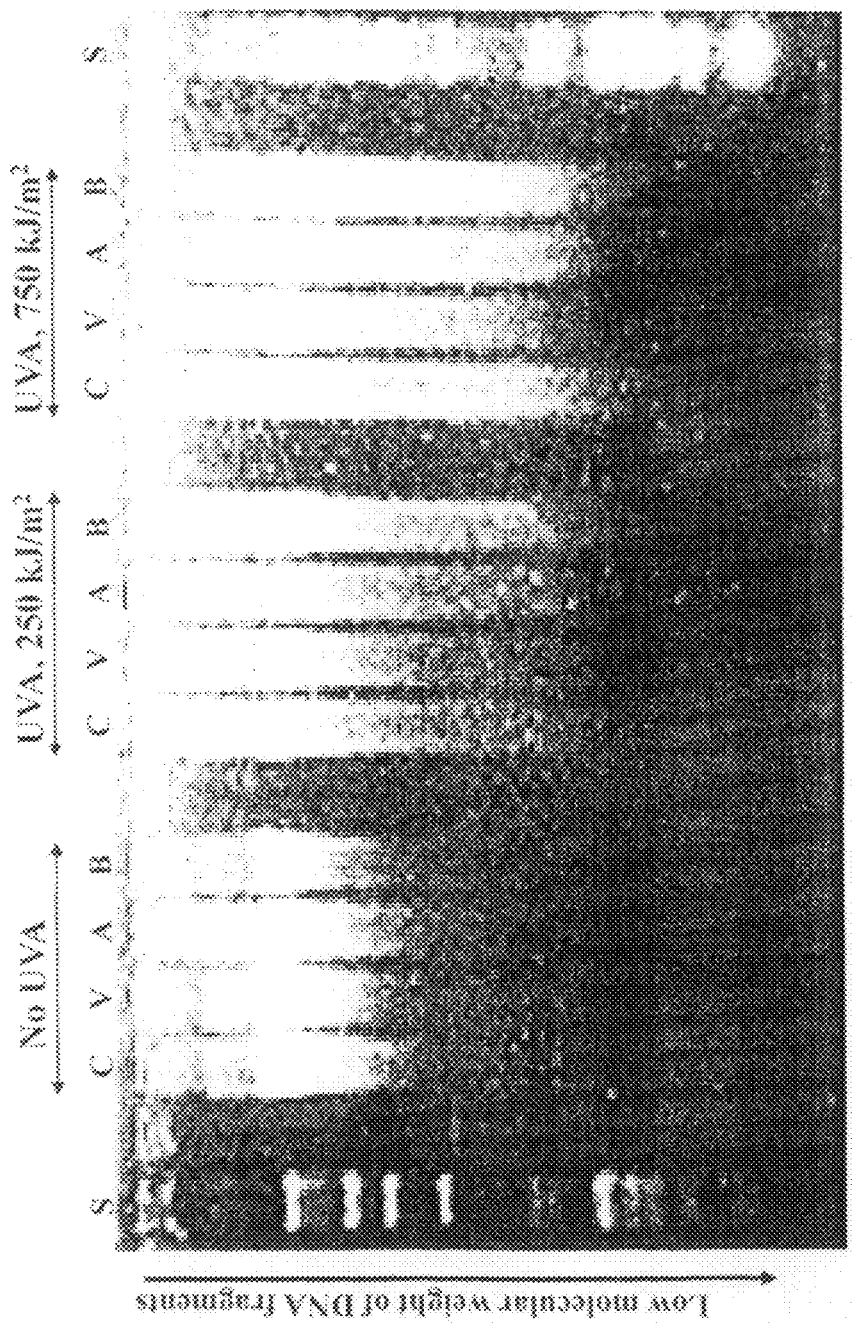
FIG. 5 illustrates the evaluation of CPD frequency following the extract treatment then UVB irradiation. Tissue treated with the extract has less photo-oxidative damage then the unprotected one as judged by the DNA smears at low molecular weight.

The inventors also measured the effects of UVA on the frequency of CPDs using neutral glyoxal gel electrophoresis. The results obtained from neutral glyoxal gel electrophoresis of DNA digested with Fpg and endo III (FIG. 5) did not conclusively demonstrate a significant efficacy of the extract at either concentration in the protection of EHS cells against DNA damage during UVA irradiation at 250 and 750 $kJ/m^2$.

Use of the Extract Plus Sunscreen

The evaluated histological parameters indicate that the addition of the extract to sunscreen (SS) does not reduce the protective effect of the sunscreen against UVA and UVB rays, and does not have a photosensitive effect on EHS tissue. But the addition of the extract to a commercial sunscreen demonstrates a surprisingly significant increase in the protection against UVA and UVB DNA damage when compared to sunscreen alone.

The results demonstrate a synergy between commercial sunscreen and the extract: the addition of the extract to sunscreen significantly increases cell DNA protection against UVB induced damage and significantly improves its protective capacity against UVA induced photo-oxidative damage. Overall, the addition of the extract to sunscreen significantly protected against UVA-induced DNA damage.

Figure 6:
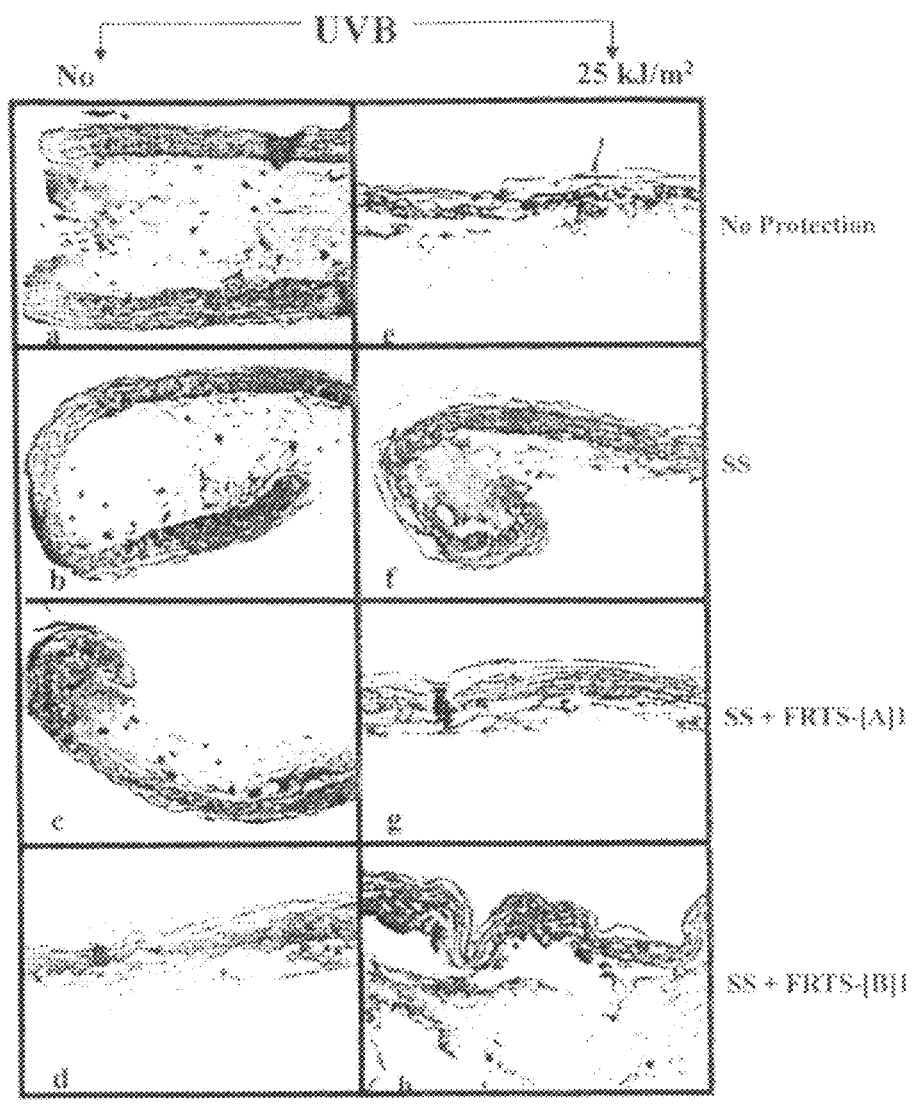
FIG. 6 illustrates the synergistic effects of the extract and sunscreen against UVB-induced tissue damage. Engineered human skins were protected with sunscreen (SPF=7.5) alone, sunscreen plus 0.01% extract, or sunscreen plus 0.1% extract for 30 minutes. Control tissues were not protected. Protected and unprotected tissues were exposed or not to 25 $kJ/m^2$ of UVB. Immediately after irradiation, biopsies were collected and stained using Masson trichrome. Stained sections were then analyzed and photographed using an optical microscope at 250× magnification.

Efficacy of the Extract Plus Sunscreen (SS-Extract) Against UVB-Induced EHS Tissue Damage As shown in FIG. 6, exposure to UVB at 25 kJ/m² induced tissue disorganization. The different strata (germinativum, granulosum, spinosum and corneum) of EHS exposed to UVB were less distinguishable from each other compared to UVB-unexposed tissues. Morphologically, differentiated keratinocytes (large cells with faint nuclei, large cytoplasm, and the presence of vacuoles) present in irradiated tissues confirmed the harmful effect of UVB (at 25 kJ/m²). FIGS. 6f, 6g and 6h illustrate that the effects of UVB exposure were prevented by sunscreen alone and by the SS-extract mixture. Indeed, the different epidermal layers of the protected EHS remained visible (FIGS. 6g and 6h) for both extract concentrations (0.01% and 0.1%) mixed with the sunscreen. In non-irradiated tissue, the SS-extract mixture did not induce structural changes to the engineered tissues (FIGS. 6c and 6d).

Efficacy of SS-Extract Against UVA-Induced EHS Tissue Damage

Figure 7:
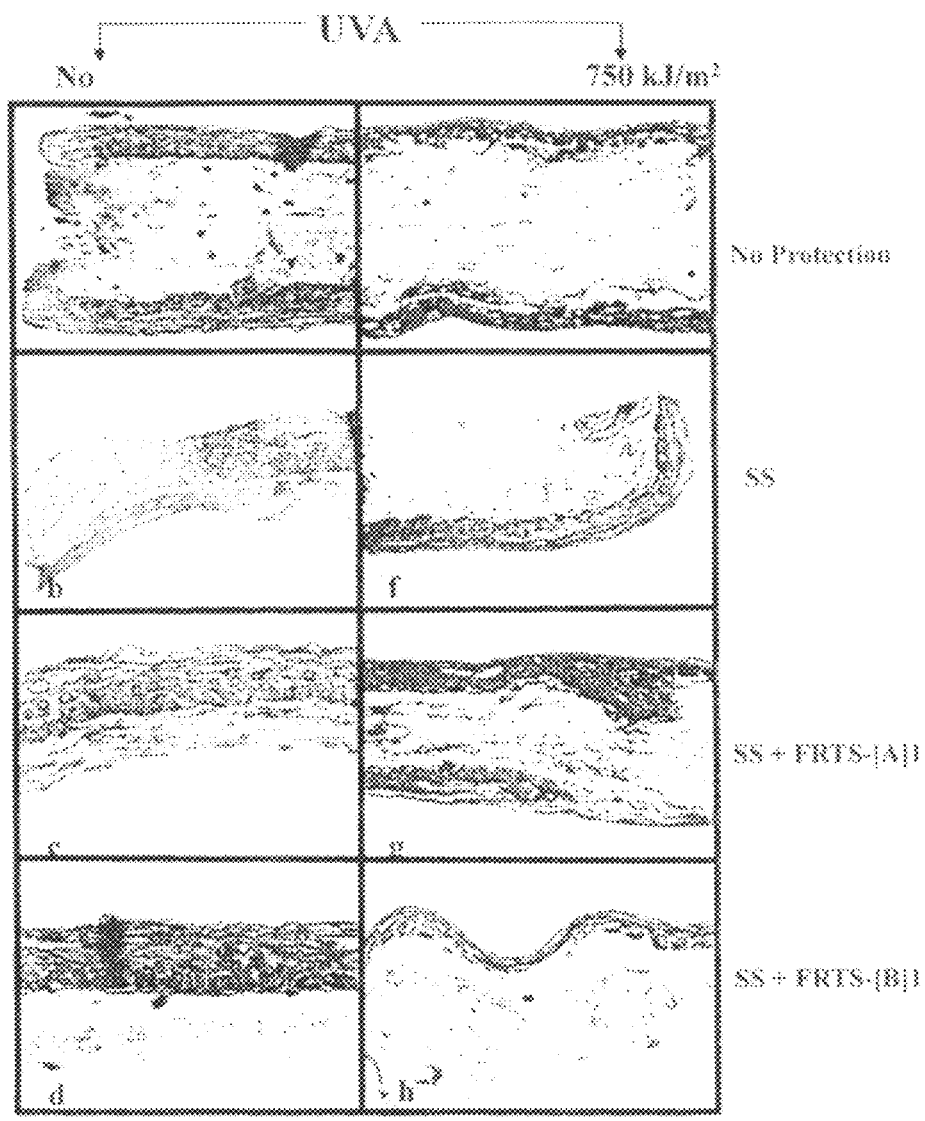
FIG. 7 illustrates the synergistic effects of the extract and sunscreen against UVA-induced tissue damage. Engineered tissues were protected with sunscreen (SPF=7.5) alone, sunscreen plus 0.01% extract, or sunscreen plus 0.1% extract for 30 minutes. Control tissues were not protected. Protected and unprotected tissues were exposed or not to 750 $kJ/m^2$ of UVA. Immediately after irradiation, biopsies were collected and stained using Masson trichrome. Stained sections were then analyzed and photographed using an optical microscope at 250× magnification.

Results presented in FIG. 7 show that exposure of unprotected tissues to 750 kJ/m² of UVA induced tissue disorganization. In irradiated tissues, there was no strata (germinativum, granulosum, spinosum and corneum) differentiation present in unprotected tissue (FIG. 7a), except the stratum corneum. The stratum corneum was very thick confirming tissue and cell necrosis due to UVA irradiation. The examination of FIGS. 7g and 7h reveals that the effects of UVA exposure were prevented by sunscreen alone and by the SS-extract mixture. Indeed, the different epidermal layers of the protected EHS remained visible (FIGS. 7f, 7g and 7h) for both extract concentrations (0.01% and 0.1%) mixed to the sunscreen. In non-irradiated tissue, the SS-extract mixture did not induce structural changes to the engineered tissues (FIGS. 7c and 7d).

Efficacy of SS-Extract Against UVB-Induced EHS DNA Damage

Figure 8:
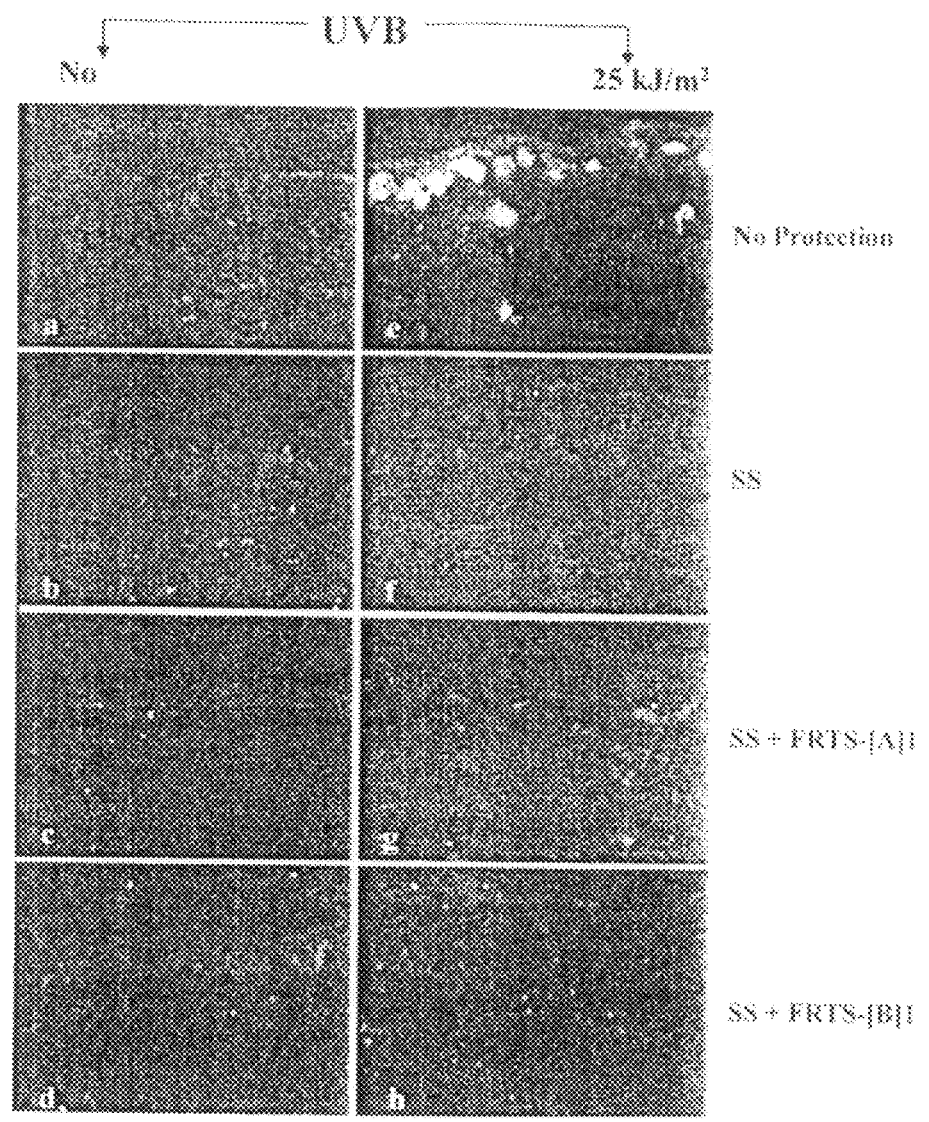
FIG. 8 illustrates the synergistic effects of the extract and sunscreen against UVB-induced CPDs. Engineered human skins were protected with sunscreen (SPF=7.5) alone, sunscreen plus 0.01% extract, or sunscreen plus 0.1% extract for 30 minutes. Control tissues were not protected. Protected and unprotected tissues were exposed or not to 25 $kJ/m^2$ of UVB. Immediately after irradiation, biopsies were collected and stained using a specific anti-CPD monoclonal antibody. Stained sections were then analyzed and photographed using a fluorescence microscope at 250× magnification.
Figure 9:
FIG. 9 illustrates the synergistic effects of the extract and sunscreen against UVB-induced CPDs. Engineered tissues were protected with sunscreen (SPF=7.5) alone, sunscreen plus 0.01% extract, or sunscreen plus 0.1% extract for 30 minutes. Control tissues were not protected. Protected and unprotected tissues were exposed or not to 25 $kJ/m^2$ of UVB. Immediately after irradiation, DNA was extracted from each sample, treated with T4endo-V and fractionated by electrophoresis (C=Control, V=Vehicle, M=Molecular weight standard, SS=Sunscreen).

Using immunofluorescence micrography, the inventors also evaluated the effect of SS-extract on CPD formation and distribution following UVB exposure. As shown in FIG. 8, exposure to UVB (25 kJ/m²) induced CPDs in the epidermal cells in the unprotected (control) EHS (FIG. 8e). CPD-positive nuclei were distributed throughout the full thickness of the epidermis, with a greater proportion of CPD-stained nuclei in the basal layer. The application of sunscreen and SS-extract at both concentrations (0.01% and 0.1%) prevented the formation of CPD in irradiated cells. In order to evaluate the synergistic effect between the extract and sunscreen, an assessment using neutral glyoxal gel electrophoresis was performed. The effects of UVB (25 kJ/m²) on the global frequency of CPDs in the epidermis of EHS are shown in FIG. 9. Analysis of DNA fragment mobility distribution demonstrated that much smaller DNA fragments were significantly present in unprotected and sunscreen protected EHS. However, when tissues were protected with a mixture of SS-extract (0.01% and 0.1%), and exposed to UVB, there was significant reduction of the CPD frequency as judged by the presence of DNA smear at high molecular weight.

Efficacy of SS-Extract Against UVA-Induced EHS DNA Damage

Figure 10:
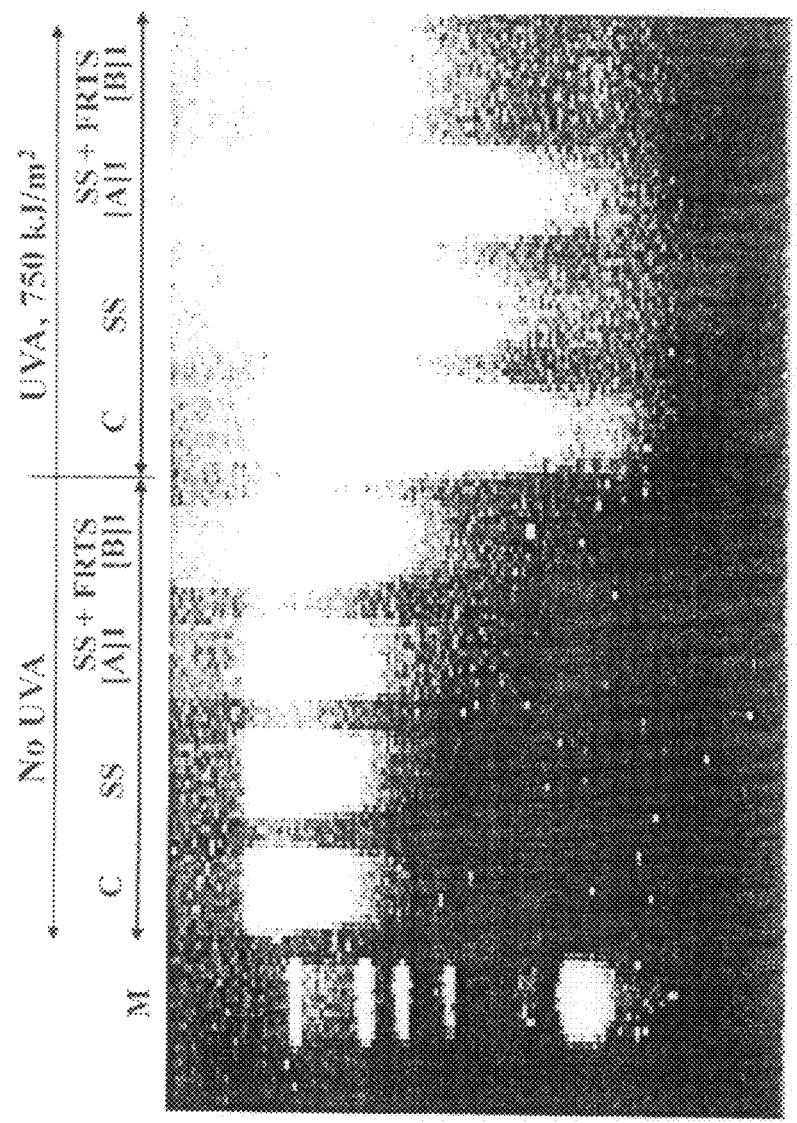
FIG. 10 illustrates the synergistic effects of the extract and sunscreen against UVA-induced photo-oxidative damage.

As UVA irradiation is known to produce a significant amount of photo-oxidative damage, an assessment using neutral glyoxal gel electrophoresis on DNA digested with Fpg and endo III was performed. Analysis of DNA fragment mobility distribution showed that much smaller DNA fragments were significantly present in unprotected tissues (FIG. 10). In tissue protected with sunscreen alone, the photo-oxidative damage was prevented as judged by the location of the DNA smear at high molecular weight. In SS-extract (0.01%) protected tissue the DNA smear was essentially present at higher molecular weight when compared to unprotected and sunscreen protected tissues.

These results illustrate that the addition of the extract to sunscreen lotion significantly improves its protective capacity against UVA induced photo-oxidative damage. Overall, the addition of the extract to sunscreen significantly protected against UVA induced DNA damage.

Use of the Extract to Repair UV-Induced Tissue and DNA Damage

Compositions comprising both concentrations of the extract (0.01% and 0.1%) demonstrated obvious improvements in the repair of EHS structural and DNA damage induced by both UVB and UVA. The inventors have demonstrated that the extract repairs UVB-induced tissue damage, very significantly promotes reparation of UVB-induced CPDs and promotes the repair of UVA-induced DNA photo-oxidative damage.

Efficacy of the Extract on Repairing UVB-Induced EHS Tissue Damage.

As shown in FIG. 11, exposure to 150 J/m² of UVB induced tissue disorganization was not repaired 3 hours following irradiation. The different strata (germinativum, granulosum, spinosum and corneum) of EHS exposed to UVB were not easily distinguishable from each other and revealed a complete absence of the basal layer. This suggested that cells in this irradiated tissue were highly affected by the UVB irradiation and were unable to repair UVB-induced damage. The same can be said of the vehicle-treated tissues, which revealed differentiated keratinocytes (large cells with faint nuclei, large cytoplasm, and the presence of vacuoles). FIG. 11 demonstrates that all UVB side effects were repaired in tissues treated with compositions comprising the extract. Indeed, the different epidermal layers of the protected EHS remained visible for both extract concentrations (0.01% and 0.1%).

Efficacy of the Extract on Repairing UVA-Induced EHS Tissue Damage.

FIG. 12 illustrates that exposure to 250 kJ/m² of UVA on unprotected (control) and vehicle-protected tissues induced tissue disorganization was not repaired 3 hours later as demonstrated by the absence of the basal layer and stratum corneum thickening. UVA-induced damage was repaired in tissues treated with compositions comprising both extract concentrations (0.01% and 0.1%), specifically in the basal layer. These histological analyses suggest that the extract promotes the reparation process in UVA-damaged tissues.

Efficacy of the Extract on Repairing UVB-Induced EHS DNA Damage.

Using immunofluorescence micrography, the effect of the extract on repairing UVB-induced CPD was evaluated. As shown in FIG. 13, the number of CPD-positive cells was very high in unprotected tissue when compared to the vehicle treated tissues. Conversely, there were no CPD positive cells following the three hours incubation in tissues treated with compositions comprising both extract concentrations (0.01% and 0.1%) indicating a significantly high (total) repair of UVB-induced CPDs. The effect of the extract on the reparation process of CPD was confirmed by neutral glyoxal gel electrophoresis analyses. Indeed, FIG. 14 reveals that the DNA smear in extract-treated tissues was localized at high molecular weight when compared to the untreated (control) and vehicle treated tissue.

Efficacy of the Extract on Repairing UVA-Induced EHS Cell Damage.

The reparation efficacy of the extract was also assessed against UVA irradiation using neutral glyoxal gel electrophoresis on DNA digested with Fpg and endo III. As shown in FIG. 15, the analysis of DNA fragment mobility distribution revealed much smaller DNA fragments in untreated (control) and vehicle treated tissues then in extract-treated EHS. Indeed, tissue protected with compositions comprising the extract (0.01% and 0.1%), the DNA smear was essentially present at higher molecular weight.

Cosmetic Efficacy (Hydration, Elasticity and Anti-Profilometry Effects)

In accordance with the present invention, cosmetic compositions comprising three different concentrations of the extract (0.01%, 0.015% and 0.02%) were developed and compared with commercially available cosmetic creams. The parameters used were hydration, elasticity and anti-profilometry effects on the skin.

Hydration data, obtained on the forehead, temple, under-eye area, cheeks and chin area of each subject, at Day 1, Day 7 and Day 28 are provided in FIG. 16. Improvements were significant versus Day 0 at all three measurement points for Group A and Group B and at Day 28 for Group C. The cosmetic composition of the present invention was associated with the highest level of statistically significant skin hydration of 17% (versus 15% and 6%) by Day 28.

FIG. 17 illustrates the evolution of Ue, which represents the immediate extensibility or ease of deformation of the skin. A reduction in the Ue signifies improvement in firmness measured by the skin's resistance to deformation. The Ue parameter reduced over time for treatment Group A by 5% at Day 1, by 7% at Day 7 and by 26% at Day 28. The reduction at Day 1 and Day 7 has significant at $p<0.05$, while the reduction at Day 28 was significant at $p<0.01$. Treatment Groups B and C also demonstrated reductions in the Ue parameter, notably by 27% for Group B and 26% for Group C at Day 28. These reductions were statistically significant at $p<0.01$.

FIG. 18 illustrates the evolution of Uf, which represents the maximal amplitude or maximal deformation of the skin, a parameter that increases with age. Treatment Group A demonstrated a significant decrease (at $p<0.05$) in maximal deformation by −5% at Day 1 versus treatment Groups B and C which did not see an improvement in this elasticity parameter at the same time of measurement. At Day 7, the maximal deformation of the skin was improved significantly (at $p<0.05$) in treatment Group A and treatment Group B (6% vs. 8%) while the improvement noted with the treatment Group C was not statistically significant. At Day 28 all three treatment groups demonstrated an improvement in the maximal deformation of the skin as follows: 25% for Group A, 28% for Group B and 27% for Group C. These improvements were statistically significant at $p<0.01$.

Skin fatigability is a parameter that generally increases with age. As seen in FIG. 19, no significant changes due to the treatments were observed for Groups A, B and C for skin fatigability at Day 1 and Day 7. However, at Day 28, a decrease in skin fatigability was noted for all three treatment groups but only the improvement seen in treatment Group A was statistically significant (at $p<0.05$).

Ur/Ue represents the net elasticity or firmness that diminishes with age and is considered to be the most important parameter in the study of the skin's elasticity. At Days 1 and 7, as shown in FIG. 20, no significant changes resulting from the treatments were observed for this parameter. However, treatment with the claimed cosmetic composition demonstrated a statistically significant increase of 5% in firmness by Day 28 ($p<0.05$).

As shown in FIGS. 21, 22 and 23, the cosmetic composition of the present invention showed statistically significant improvements in the following wrinkle parameters compared to baseline as early as Day 1 of treatment which increased in magnitude with treatment and remained significant at Day 28: area of wrinkles −12% at Day 1 and −17% at Day 28 ($p<0.01$, each) (FIG. 21); total length of wrinkles −11% at Day 1 and −13% at Day 28 ($p<0.01$, each) (FIG. 22); and mean length of wrinkles −5% at Day 1 and −11% at Day 28 ($p<0.05$ and $p<0.01$) (FIG. 23). Significant improvement of −7% ($p<0.01$) in the total number of wrinkles at Day 1 was also observed with the cosmetic composition of the present invention as seen in FIG. 24. In contrast, treatment with the other two prestige product lines improved wrinkle parameters but the improvements were only 18 to 47% of the magnitude of the improvements seen for the cosmetic composition of the present invention and were not statistically significant compared to baseline.

With respect to the class of the wrinkles, and as shown in FIGS. 25, 26 and 27, the cosmetic composition of the present invention non-significantly reduced the number of Class 3 (profound) wrinkles by −7% as early as Day 1 and was the only treatment that produced a significant −13% ($p<0.05$) reduction from baseline in Class 3 wrinkles at Day 28 of treatment and a −9% ($p<0.01$) significant reduction in Class 2 (moderate) wrinkles at Day 1 of treatment. The other two comparative prestige product lines increased Class 3 wrinkles at Day 28 by +7% and +5%, respectively.

No significant results were seen in the reductions of the number of wrinkles of Class 1 (fine) for any of the three treatments. Statistical analysis of the depth of the wrinkles revealed no significant reduction over time for any of the three treatments.

Synergistic Effect with Spilanthol

Spilanthol is an *Acmella oleracea* extract that is known to inhibit contractions in subcutaneous muscles and to be used as an anti-wrinkle product. The use of the spilanthol with the photosynthetic cell extract causes a synergistic effect in an anti-wrinkle cosmetic composition.

Example 1

Preparation of Engineered Human Skin

Skin donors were healthy women, 15 to 20 years of age. Keratinocytes and fibroblasts were isolated from UV-unexposed normal human skin biopsies following breast reductive surgeries as previously described. Engineered human skins (EHS) were produced by mixing calf skin type I and type III collagen (2 mg/ml, Sigma) with normal human fibroblasts ($1.5 \times 10^6$ cells/ml) to produce the dermis. Tissues were cultured in 5% fetal calf serum-supplemented medium for 4 days and then seeded with keratinocytes ($9 \times 10^4/cm^2$) to obtain EHS. EHS were grown under submerged conditions for seven days and were then raised to an air-liquid interface for five more days to allow the differentiation of the epidermis into the different strata. Each series was conducted using keratinocytes and fibroblasts isolated from the same skin biopsy.

Extract Treatment and UV Irradiation.

Two concentrations of the extract (A=0.1% and B=0.01%) were tested. The extract vehicle alone (at the same concentration found in extract treatments) served as the first control. Normal untreated tissue served as the second control. Volumes of 60 □l of the extract or its vehicle were applied on the stratum corneum of EHS 30 min before irradiation. Three experimental conditions (untreated, vehicle-treated or extract-treated) were tested. Prior to irradiation, the culture medium was replaced by the irradiation medium (DME supplemented with bovine pituitary extract), without phenol red and hydrocortisone, in order to avoid UV-induced formation of medium-derived toxic substances. Petri dishes containing EHS were placed on ice and uncovered to allow direct exposure of EHS to UV rays. Three doses of UVA (0, 250 and 750 $kJ/m^2$) and three doses of UVB (0, 10 and 25 $kJ/m^2$) were used to irradiate treated and untreated EHS. The UVA source was a neon BLB light 45 cm (number BL-18, 15 W UV, Ateliers Albert Inc., Montreal, QC) with an emission spectrum containing a peak at approximately 360 nm. The UVB source was a FS20T12/UVB/BP lamp (Philips, Somerset, N.J.) with an emission spectrum containing a peak between 290 and 320 nm. All administrated doses were monitored using a YSI Kettering 65A radiometer (Yellow Springe Instruments, Ohio).

Histological and Immunohistochemical Analyses Following UV Exposure.

Immediately after irradiation, biopsies were taken from each EHS. They were either fixed with Bouin's solution and then embedded in paraffin, or directly embedded at optimal cutting temperatures, frozen in liquid nitrogen, and stored at −80° C. until use. Thin sections (4 □m) of the paraffin embedded biopsies were stained with Masson Trichrome to evaluate the structure of the tissue as described elsewhere. For CPD evaluation, only tissues irradiated with UVB were used. For this purpose, thin cryostat sections (4 □m) of UVB-irradiated frozen biopsies were incubated for 45 min at room temperature with specific mouse monoclonal CPD antibody (Biomedical Technologies, Stoughton, Calif.). The CPD antibody reacts specifically with UV-induced thymidine dimers in double or single-stranded DNA. Sections were then incubated in fluorescein isothiocyanate-conjugated (FITC) to goat anti-mouse immunoglobulin (Chemicon, Temecula, Calif.), diluted 1:100, for 30 min at room temperature. The sections were extensively washed with phosphate buffered saline between incubations. They were mounted with coverslips in 50% glycerol mounting medium and observed using epifluorescence microscopy and photographed.

Molecular Analyses Following Solar UV Radiation Exposure.

Immediately after irradiation, epidermal cells were isolated as previously described. After homogenization, cells were centrifuged and cellular pellets were re-suspended in 2 ml of 0.15 M NaCl; 0.005 M EDTA pH 7.8 and 2 ml of 0.02 M Tris-HCl pH 8.0; 0.02 M NaCl; 0.02 M EDTA pH 7.8; 1% SDS. DNA was purified as previously described, and used to evaluate the global frequency of CPD photoproducts that are specific to UVB irradiation, and photo-oxidative damage that is specific to UVA irradiation.

To specifically cleave CPDs, 10 µg of UV-irradiated DNA was dissolved in 50 µL $H_2O$. The following solution was added to each DNA sample: 50 µL of a solution containing 10 µL of 10× dual buffer (10× dual buffer: 500 mM Tris-HCl pH 7.6, 500 mM NaCl, and 10 mM EDTA), 0.1 µL of 1 M DTT, 2 µL of 5 mg/mL BSA, a saturating amount of $T_4$ endonuclease V, and completed with $H_2O$ to a final volume of 50 µL. The reaction was performed at 37° C. for 1 h. To specifically cleave photo-oxidative damage, 10 µg of UV-irradiated DNA was dissolved in 50 µl of water and 50 µl of 2× Nth protein buffer (100 mM tris-HCl pH 7.6, 200 mM KCl, 2 mM EDTA, 0.2 mM dithiothreitol, 200 µg/ml bovine serum albumin). Enzymes (nth and fpg) were added to 5 µl of dilution buffer (50 mM tris-HCl pH 7.6, 100 mM KCl, 1 mM EDTA, 0.1 mM dithiothreitol, 500 µg/ml bovine serum albumin, 10% (v/v) glycerol), the total digestion volume was 105 µl. The samples were incubated at 37° C. for 60 min. Following ethanol precipitation, digested DNA was re-suspended to a final concentration of 1 µg/µL.

The global frequency for each class of photoproducts was determined with neutral agarose gel electrophoresis of glyoxal/dimethylsulfoxide-denatured genomic DNA as previously described. Briefly, 5 µg/10 µl of treated DNA was dissolved in distilled water and 2 µL of 100 mM sodium phosphate, pH 7.0, 3.5 µL of 6 M glyoxal (Sigma Chemical Co., St. Louis, Mo.), and 10 µL of dimethylsulfoxide was added. DNA samples were incubated at 50° C. for 1 h. Prior to loading, 3.8 µL of loading buffer (10 mM sodium phosphate, pH 7.0; 50% glycerol; 0.25% xylene cyanol FF) were added. The gels were run in 10 mM sodium phosphate pH 7.0, running buffer at 3-4 volts/cm with constant buffer circulation. The gels were stained for 2 h in a solution of 1×SYBR® Gold nucleic acid gel stain (S-11494) (Molecular Probes, Eugene, Oreg.) in TAE pH 8.0 and photographed. The overall adduct frequency was estimated following the enzymatic conversion of DNA photoproducts to single-strand breaks. The migration of the DNA fragments through the agarose gel allows for their separation according to their molecular weight—the smaller the fragment, the greater the distance of migration. Willis et al. have shown that when a randomly cleaved DNA molecule is gel-fractionated, the mobility of each fragment is proportional to the log of the molecular weight throughout the middle of the mobility range. It is, therefore, possible to calculate the approximate mass of each DNA smear by estimating the molecular weight at the highest intensity of the DNA staining dye. The numbers obtained were divided by 2 (as each fragment contains one photoproduct at each end) and expressed as number of lesions per megabase (Mb).

Example 2

Preparation of Engineered Human Skin

Skin donors were healthy women, 15 to 20 years of age. Keratinocytes and fibroblasts were isolated from UV-unexposed normal human skin biopsies following breast reductive surgeries as previously described. Engineered human skins were produced as described above.

Sunscreen Plus Extract Treatment and UV Irradiation.

Two concentrations of the extract (0.01% and 0.1%) were mixed v/v separately with SPF 15 sunscreen (SS). After mixing with the extract (0.01% and 0.1%), the obtained sunscreen had a SPF of 7.5. The vehicle (sunscreen with a SPF 7.5) served as a control. Normal unprotected tissue served as a second control. Volumes of 60 µl of SS-extract or SS-vehicle were applied on the stratum corneum of EHS for 30 minutes before irradiation. The irradiation procedures were the same as described above. Two doses of UVA (0 and 750 kJ/m$^2$) and two doses of UVB (0 and 25 kJ/m$^2$) were used to irradiate protected and unprotected EHS.

Histological and Immunohistochemical Analyses Following UV Exposure.

Immediately after irradiation, biopsies were taken from each EHS. They were either fixed with Bouin's solution and embedded in paraffin, or directly embedded at optimal cutting temperature, frozen in liquid nitrogen, and stored at −80° C. until use. Histological (Masson trichrome staining) and immunofluorescence (CPDs) analyses were performed as described above. For CPD evaluation, only tissue irradiated with UVB was used.

Molecular Analyses Following UV Exposure.

Immediately after irradiation, epidermal cells were isolated and used to extract DNA. Purified DNA was used to evaluate the global frequency of CPD photoproducts that are specific to UVB irradiation, and photo-oxidative damage that is specific to UVA irradiation. For this purpose, the inventors used the different steps described above.

Example 3

Preparation of Engineered Human Skin

Skin donors were healthy women, 15 to 20 years of age. Keratinocytes and fibroblasts were isolated from UV-unexposed normal human skin biopsies following breast reductive surgeries as previously described. Engineered human skins were produced as described above.

Tissues Exposure to UV Followed by Treatment with the Extract.

After their production, EHS was exposed to ultraviolet (UVA or UVB) sources. One dose (250 kJ/m$^2$) of UVA and one dose (150 J/m$^2$) of UVB were used to irradiate unprotected EHS. The irradiation procedures were the same as described in section 1.2. Immediately after irradiation tissues were treated with the extract. Volumes of 60 µl of the extract or its vehicle were applied on the stratum corneum of EHS for 3 hours prior to analysis.

Histological and Immunohistochemical Analyses.

Following the incubation period, biopsies were taken from each EHS. They were either fixed with Bouin's solution and embedded in paraffin, or directly embedded at optimal cutting temperature, frozen in liquid nitrogen, and stored at −80° C. until use. Histological (Masson trichrome staining) and immunofluorescence (CPDs) analyses were performed as described above. For CPD evaluation, only tissues irradiated with UVB were used.

Molecular Analyses Following UV Exposure.

Following the incubation period, epidermal cells were isolated and used to extract DNA. Purified DNA was used to evaluate the global frequency of CPD photoproducts that are specific to UVB irradiation, and photo-oxidative damage that is specific to UVA irradiation.

Example 4

In a comparative cosmetic efficacy study (single-blind, mono-centric, parallel group design) of 72 healthy female volunteers aged 35 to 72 years (mean age 54.6 years), the efficacy of the present cosmetic composition was compared to that of two leading commercial anti-aging brands over a 28 day period of use. Efficacy parameters included: effect on skin appearance, hydration, elasticity, and profilometry (anti-wrinkle effect).

Each volunteer was provided with three formulations of the present cosmetic composition comprising 0.01%, 0.015% and 0.02% of the extract, in combination with non-active ingredients, along with application instructions, to be used over a 28-day period. Measurements were taken on Day 0, Day 1, Day 7 and Day 28. Hydration was assessed using a Corneometer®, elasticity was assessed using a Cutometer® and profilometry measurements were taken from silicone replicates of the eye contour zones using a Visia-CR Imaging system. Verification of product usage was determined by weighing the product samples.

On the first visit (Day 0 or D0) the volunteers randomly received the containers of one of the three test treatments (day cream, eye lotion and night cream), a follow-up sheet to be completed after every application and a self-evaluation questionnaire to be completed after 28 days of treatment.

The volunteers were instructed to apply, each morning, after having washed their face and hands (with their regular cleansing products) a sufficient quantity of the eye lotion to cover the eye contour area including the crows' feet area of their face. After the eye lotion was well penetrated, the volunteers had to apply the day cream, in sufficient quantities, to cover their entire face avoiding the eye contour area.

Additionally, the volunteers were instructed to apply, every evening, enough of the night cream to cover their entire face avoiding the eye contour area.

The use of all other skin care products (except for regular cleansing products and makeup) was prohibited during the study. Changes regarding the brand of their regular facial cleanser or makeup products were not permitted during the week prior the commencement of the study nor during the study.

On Day 0, twelve digital photographs of the face (full front, right profile and left profile, in four different imaging modes: Standard, Cross Polarized, UV. and Parallel Polarized), were taken using the Visia-CR Imaging System. Subsequently, the study was conducted in a laboratory room with controlled temperature (22° C.±3) and relative humidity (30%±5). After 15 minutes of stabilisation in the controlled room, measurements of hydration using Corneometer®, measurements of elasticity using Cutometer®, and Profilometry by silicone imprints of eye contour zones before treatment were taken.

Measurements taken at D0 were repeated at D1, D7 and D28 in the same manner as described above. At D1, D7 and D28 the volunteers had to return their completed daily logs. They were also to return to the tab the sample containers with the unused portion of the test products. The unused portion of the sample containers and daily logs (use diaries) were intended for verification of the volunteers' adherence to the protocol.

Hydration.

Epidermal moisture of the stratum corneum can be assessed by non-invasive in vivo instrumental testing methods based on the electric properties of the skin, the electrical capacitance. The stratum corneum is a dielectric corpus and all changes in its hydration status are reflected by changes in the electric capacitance, expressed in arbitrary units by the Corneometer®.

Elasticity.

The skin's appearance is related to and highly affected by its elastic properties. The elasticity of the skin is subject to change with the use of cosmetic products. Changes in the mechanic and viscoelastic properties of the skin reflect the elasticity of the skin. The elasticity related parameters were measured by Cutometer® SEM 575 (Courage and Khazaka, Germany). The instrument is equipped with a probe (2 mm aperture in diameter) that includes a controlled suction (vacuum of 400 mbar) on the skin with four repetitions of 1 second. Two measurements were taken from the middle of each cheek.

The results on each measurement site are expressed as the following parameters:

Ue="extensibility" or "immediate elastic deformation" due to the application of vacuum Uf="total amplitude" or "maximum amplitude" of the skin (Ue+Uv)

Ur="tonicity"

Ur/Ue="net elasticity" or "pure elasticity" or firming

Finally, after four aspirations, the Cutometer® provides a measure of the skin's "fatigability".

Anti-Wrinkle Effect.

Imprints (negatives of the skin surface) of the eye contour zones were obtained by applying silicone polymer onto the "crows' feet" area of the eye contour zone, while the volunteer maintained an upright but sitting position. The silicone polymer used for this study consisted of Silflo® (silicone dental impression material of Flexico-Developments Ltd., Potters Bar, England).

Imprints of the crows' feet were analyzed by a computerized digital image processing system coupled to Quantirides® software (designed by Monoderm, Monaco) to obtain the topography of the skin. This standard technique is based on measuring the shadows cast when an incident light is inclined at an angle of 35° on the replica.

The analyzed parameters were the total area of wrinkled skin, the number and the mean depth of the depressions due to the cutaneous relief, and depth of deep and medium wrinkles. The wrinkles were differentiated by depth (Class 1 for 0-55 µm; Class 2 for 55-100 µm; and Class 3 for 110-800 µm) before and after treatment in order to better demonstrate the efficacy of a given product.

What is claimed:

1. A method to provide protection to skin against oxidative damage caused by ultra-violet (UV) radiation comprising applying to the skin an effective amount of a cosmetic composition comprising:
   a functional thylakoids-containing photosynthetic cell extract (PCE), wherein the PCE is present in an amount from about 0.01% to about 0.1% based upon total weight of the composition:
   an anti-UV effective amount of a sunscreen agent; and
   an acceptable carrier.

2. The method of claim 1, wherein the oxidative damage includes lipid peroxidation.

3. The method of claim 1, wherein the oxidative damage includes erythrocyte haemolysis.

4. The method of claim 1, wherein the oxidative damage includes DNA damage.

5. The method of claim 1, wherein the composition is formulated for topical application.

6. The method of claim 1, wherein the carrier of the composition is selected from the group consisting of fats, hydrophilic or lipophilic gelling agents and fillers.

7. The method of claim 1, wherein the extract is non-lyophilized and formulated in a liquid composition.

8. The method of claim 1, wherein the extract is a lyophilized extract reconstituted in a solution compatible with topical administration.

9. The method of claim 8, wherein the lyophilized extract is in water, physiological saline or propylene glycol.

10. The method of claim 8, wherein the lyophilized extract is in a solid composition.

11. The method of claim 1, wherein the UV radiation is UVA radiation.

12. The method of claim 1, wherein the UV radiation is UVB radiation.

* * * * *

UNITED STATES PATENT AND TRADEMARK OFFICE
CERTIFICATE OF CORRECTION

PATENT NO. : 10,045,934 B2
APPLICATION NO. : 13/261472
DATED : August 14, 2018
INVENTOR(S) : Boulet et al.

Page 1 of 1

It is certified that error appears in the above-identified patent and that said Letters Patent is hereby corrected as shown below:

On the Title Page

Item (30) under Foreign Application Priority Data, delete "April 2, 2011" and substitute therefor
— April 12, 2010 —

Signed and Sealed this
Eleventh Day of February, 2020

Andrei Iancu
*Director of the United States Patent and Trademark Office*